US012790635B2

(12) United States Patent
Wang et al.

(10) Patent No.: US 12,790,635 B2
(45) Date of Patent: Nov. 10, 2026

(54) DETECTION METHOD OF ANTIMICROBIAL SUSCEPTIBILITY TEST BASED ON FLUORESCENT D-AMINO ACID METABOLIC LABELING

(71) Applicant: RENJI HOSPITAL, SHANGHAI JIAO TONG UNIVERSITY SCHOOL OF MEDICINE, Shanghai (CN)

(72) Inventors: Wei Wang, Shanghai (CN); Chaoyong Yang, Shanghai (CN)

(73) Assignee: RENJI HOSPITAL, SHANGHAI JIAO TONG UNIVERSITY SCHOOL OF MEDICINE, Shanghai (CN)

( * ) Notice: Subject to any disclaimer, the term of this patent is extended or adjusted under 35 U.S.C. 154(b) by 799 days.

(21) Appl. No.: 17/995,149

(22) PCT Filed: Mar. 25, 2021

(86) PCT No.: PCT/CN2021/083051
§ 371 (c)(1),
(2) Date: Sep. 30, 2022

(87) PCT Pub. No.: WO2021/203981
PCT Pub. Date: Oct. 14, 2021

(65) Prior Publication Data

US 2024/0240224 A1 Jul. 18, 2024

(30) Foreign Application Priority Data

Apr. 7, 2020 (CN) ......................... 202010263592.1
Mar. 19, 2021 (CN) ......................... 202110295193.8

(51) Int. Cl.
*C12Q 1/18* (2006.01)
*G01N 21/64* (2006.01)
*G01N 33/58* (2006.01)

(52) U.S. Cl.
CPC ........... *C12Q 1/18* (2013.01); *G01N 21/6428* (2013.01); *G01N 33/582* (2013.01); *G01N 2021/6439* (2013.01)

(58) Field of Classification Search
CPC ..... C12Q 1/18; G01N 33/582; G01N 21/6428
USPC ........................................................... 435/32
See application file for complete search history.

(56) References Cited

U.S. PATENT DOCUMENTS

2016/0222430 A1 8/2016 Van Nieuwenhze et al.
2019/0024135 A1 1/2019 Van Nieuwenhze et al.

FOREIGN PATENT DOCUMENTS

CN 103074313 A 5/2013
CN 110643686 A 1/2020
CN 111458313 A 7/2020
WO WO-2018119439 A1 * 6/2018 ............... C12Q 1/18

OTHER PUBLICATIONS

Wang, et al. "Assessing the viability of transplanted gut microbiota by sequential tagging with D-amino acid-based metabolic probes." Nature Communications, Mar. 21, 2019, 8 pages.
International Search Report and Written Opinion of International Application No. PCT/CN2021/083051, mailed on Jun. 23, 2021, 15 pages, Partial Translation.
Syal et al., "Current and emerging techniques for antibiotic susceptibility tests," Theranostics, 2017, vol. 7(7): pp. 1795-1805.
Manina et al., "Stress and Host Immunity Amplify *Mycobacterium tuberculosis* Phenotypic Heterogeneity and Induce Nongrowing Metabolically Active Forms," Cell Host & Microbe, 2015, vol. 17: pp. 32-46.
Hou et al., "Time lapse investigation of antibiotic susceptibility using a microfluidic linear gradient 3D culture device," Lab Chip, 2014, vol. 14: pp. 3409-3418.
Choi et al., "A rapid antimicrobial susceptibility test based on single-cell morphological analysis," Science Translational Medicine, 2014, vol. 6(267): pp. 1-14.
Baletkin et al., "Antibiotic susceptibility testing in less than 30 min using direct single-cell imaging," Proceedings of the National Academy of Sciences, 2017, vol. 14(34): pp. 9170-9175.
Hou et al., "Direct detection and drug-resistance profiling of bacteremias using inertial microfluidics," Lab on a Chip, 2015, vol. 115(10): pp. 2297-2307, Abstract Only.
Bhattacharyya et al., "Simultaneous detection of genotype and phenotype enables rapid and accurate antibiotic susceptibility determination," Nature Medicine, 2019, vol. 25(12): pp. 1858-1864, Abstract Only.
Longo et al., "Rapid detection of bacterial resistance to antibiotics using AFM cantilevers as nanomechanical sensors," Nature Nanotechnology, 2013, vol. 8(7): pp. 552-526, Abstract Only.
Tao et al., "Metabolic-Activity-Based Assessment of Antimicrobial Effects by D2O-Labeled Single-Cell Raman Microspectroscopy," Analytical Chemistry, 2017, vol. 89(7): pp. 4108-4115, Abstract Only.
Hong et al., "Antibiotic Susceptibility Determinatino within One Cell Cycle at Single-Bacterium Level by Stimulated Raman Metabolic Imaging," Analytical Chemistry, 2018, vol. 90(6): pp. 3737-3743.

(Continued)

*Primary Examiner* — Melenie L Gordon
*Assistant Examiner* — Grant C Currens
(74) *Attorney, Agent, or Firm* — Heslin Rothenberg Farley & Mesiti P.C.

(57) ABSTRACT

The invention relates to a method for detecting antimicrobial susceptibility test based on fluorescent D-type amino acid metabolic marker, which uses the bacterial solution cultivated by the mixture of fluorescent D-type amino acid metabolic marker and antibiotic solution to obtain the minimum inhibitory concentration of antibiotics according to its fluorescent signal intensity.

13 Claims, 23 Drawing Sheets

(56) References Cited

OTHER PUBLICATIONS

Yang et al., "Rapid Antibiotic Susceptibility Testing of Pathogenic Bacteria Using Heavy-Water-Labeled Single-Cell Raman Spectroscopy in Clinical Samples," Analytical Chemistry, 2019, vol. 91(9):pp. 6296-6303.

Pidgeon et al., "Metabolic Profiling of Bacteria by Unnatural C-terminated D-Amino Acids," Angewandte Chemie International Edition, 2015, vol. 54(21):pp. 6158-6162, Abstract Only.

Kuru et al., "Synthesis of fluorescent D-amino acids and their use for probing peptidoglycan synthesis and bacterial growth in situ," Nature Protocols, 2015, vol. 10(1): pp. 33-52.

* cited by examiner

| Cephalosporins /Gram negative bacteria | *E. Coli* | | | | | | | *A. Baumannii* | | | |
|---|---|---|---|---|---|---|---|---|---|---|---|
| | *Ec11* | | *Ec13* | | *Ec ATCC 25922* | | | *Ab16* | | *Ab19* | |
| | VITEK | FaAST | VITEK | FaAST | CLSI QC range | VITEK | FaAST | VITEK | FaAST | VITEK | FaAST |
| Levofloxacin | ≤0.25 | 0.5 | 4 | 4 | 0.008-0.06 | ≤0.25 | **≤0.25** | 16 | 32 | ≤0.25 | 0.5 |
| Tigecycline | ≤0.25 | ≤0.25 | ≤0.25 | ≤0.25 | 0.03-0.25 | ≤0.25 | **≤0.25** | ≤0.25 | ≤0.25 | ≤0.25 | ≤0.25 |
| Imipenem | ≤0.25 | 1 | 16 | >128 | 0.06-0.25 | *≤0.25* | *1* | 32 | 64 | ≤0.25 | 1 |
| Amikacin | 4 | 2 | 2 | 1 | 0.5-4 | 1 | 2 | ≥256 | ≥256 | 2 | 2 |
| Polymyxin B | 2 | 2 | 8 | 32 | 0.25-2 | 2 | 2 | - | - | - | - |

| Cephalosporins /Gram negative bacteria | *P. aeruginosa* | | | | | | | *K. pneumoniae* | | | |
|---|---|---|---|---|---|---|---|---|---|---|---|
| | *Pa2* | | *Pa3* | | *Pa ATCC 27853* | | | *Kp6* | | *Kp9* | |
| | VITEK | FaAST | VITEK | FaAST | CLSI QC range | VITEK | FaAST | VITEK | FaAST | VITEK | FaAST |
| Levofloxacin | 0.5 | 1 | *0.5* | *1* | 0.5-4 | 0.5 | 0.5 | ≤0.25 | 1 | 32 | 128 |
| Tigecycline | - | - | - | - | - | - | - | ≤0.25 | 0.25 | 0.5 | 0.25 |
| Imipenem | *1* | 2 | 32 | ≥256 | 1-4 | 2 | 4 | ≤0.25 | 1 | 128 | 256 |
| Amikacin | 2 | 0.5 | 4 | 8 | 1-4 | 2 | 4 | 0.5 | 0.5 | ≥256 | ≥256 |
| Polymyxin B | - | - | - | - | - | - | - | 0.5 | 1 | 8 | 32 |

FIG. 27

| Antibiotics/ gram positive bacteria | *S. Aureus* | | | | | | | *E. faecium* | | | | | | |
|---|---|---|---|---|---|---|---|---|---|---|---|---|---|---|
| | Sa22 | | Sa23 | | Sa ATCC 29213 | | | Ef 26 | | Ef 26 | | Ef ATCC 29212 | | |
| | VITEK | FaAST | VITEK | FaAST | CLSI QC range | VITEK | FaAST | VITEK | FaAST | VITEK | FaAST | CLSI QC range | VITEK | FaAST |
| Levofloxacin | 32 | 32 | 1 | 1 | 0.06-0.5 | ≤0.25 | 0.5 | ≥256 | 64 | ≥256 | 64 | 0.25-2 | 1 | 1 |
| Vancomycin | 1 | 2 | 1 | 2 | 0.5-2 | 1 | 1 | 0.5 | 0.25 | ≥256 | 32 | 1-4 | 2 | 2 |
| Tekoplanin | 0.5 | 1 | 0.5 | 1 | 0.25-1 | ≤0.25 | 0.25 | 0.5 | 0.25 | *16* | 32 | 0.25-1 | ≤0.25 | 0.5 |
| Linezolid | 2 | 1 | 8 | 8 | 1-4 | 2 | 2 | 2 | 2 | 2 | 2 | 1-4 | 2 | 2 |
| Erythromycin | - | - | - | - | - | - | - | 0.25 | 0.25 | ≥256 | ≥256 | 1-4 | 2 | 2 |

FIG. 28

| **Cephalosporins /Gram negative bacteria** | ***E. Coli*** | | | | | | | ***A. baumannii*** | | | |
|---|---|---|---|---|---|---|---|---|---|---|---|
| | *Ec11* | | *Ec13* | | *Ec ATCC25922* | | | *Ab16* | | *Ab19* | |
| | VITEK | FaAST | VITEK | FaAST | CLSI QC range | VITEK | FaAST | VITEK | FaAST | VITEK | FaAST |
| Cefepime | ≤0.25 | 0.5 | *>64* | *>128* | 0.016-0.12 | ≤0.25 | 0.25 | 128 | 64 | 1 | 1 |
| Cefuroxime axtetil | 4 | 8 | ≥256 | ≥256 | 2-8 | 4 | 8 | - | - | - | - |
| SCF | ≤0.25 | 1 | ≥256 | ≥256 | - | 0.5 | 1 | 64 | 128 | 1 | 1 |

| **Cephalosporins /Gram negative bacteria** | ***P. aeruginosa*** | | | | | | | ***K. pneumoniae*** | | | |
|---|---|---|---|---|---|---|---|---|---|---|---|
| | *Pa2* | | *Pa3* | | *Pa ATCC 27853* | | | *Kp6* | | *Kp9* | |
| | VITEK | FaAST | VITEK | FaAST | CLSI QC range | VITEK | FaAST | VITEK | FaAST | VITEK | FaAST |
| Cefepime | 1 | 1 | *8* | *4* | 0.5-4 | 2 | 2 | ≤0.25 | 0.5 | ≥256 | ≥256 |
| Cefuroxime axtetil | - | - | - | - | - | - | - | 2 | 4 | ≥256 | ≥256 |
| SCF | 4 | 8 | 8 | 16 | - | 4 | 4 | ≤0.25 | 0.5 | ≥256 | ≥256 |

FIG. 29

*S. aureus*

| **Antibiotics /*S. aureus*** | ***Sa22*** | | ***Sa23*** | | ***Sa24*** | | ***Sa25*** | |
|---|---|---|---|---|---|---|---|---|
| | BMD | FaAST | BMD | FaAST | BMD | FaAST | BMD | FaAST |
| Oxacillin | 1024 | 1024 | 0.5 | 2 | 0.5 | 1 | 8 | 4 |

| **Antibiotics /*S. aureus*** | ***Sa31*** | | ***Sa5*** | | ***Sa59*** | | ***Sa398*** | |
|---|---|---|---|---|---|---|---|---|
| | BMD | FaAST | BMD | FaAST | BMD | FaAST | BMD | FaAST |
| Oxacillin | 1024 | 1024 | 512 | 512 | 64 | 128 | 0.5 | 4 |

| **Antibiotics /*S. aureus*** | ***Sa ATCC 43300*** | | | ***Sa ATCC 29213*** | | |
|---|---|---|---|---|---|---|
| | CLSI QC range | BMD | FaAST | CLSI QC range | BMD | FaAST |
| Oxacillin | >4 | 64 | 32 | 0.12-0.5 | 0.25 | 1 |

FIG. 30

DETECTION METHOD OF ANTIMICROBIAL SUSCEPTIBILITY TEST BASED ON FLUORESCENT D-AMINO ACID METABOLIC LABELING

CROSS REFERENCE TO RELATED APPLICATIONS

This application is a U.S. National Filing Phase filing under 35 U.S.C. § 371 of International Application PCT/CN2021/083051, filed on Mar. 25, 2021, and published on Oct. 14, 2021 as WO 2021/203981, and claims priority to Chinese Patent Application No. 202010263592.1 field on Apr. 7, 2020 and Chinese Patent Application No. 202110295193.8 filed on Mar. 19, 2021. The entire contents of each of these prior applications are hereby incorporated herein by reference.

TECHNICAL FIELD

The invention relates to an evaluation method of bacterial metabolic activity and a detection method of antimicrobial susceptibility test, in particular to a detection method of antimicrobial susceptibility test based on fluorescent D-amino acid metabolic markers, which is used to rapidly test or evaluate the antibacterial effect of antibacterial agents or bacterial metabolic activity, such as antibiotics, on clinically isolated bacterial strains to guide clinical drug use.

BACKGROUND TECHNOLOGY

With the extensive use of antibiotics in medical and aquaculture industries, especially the extensive use of broad-spectrum antibiotics, the problem of bacterial resistance has become increasingly prominent, and even super bacteria that can resist almost all antibiotics have emerged. The emergence and spread of bacterial drug resistance has aroused widespread concern all over the world, and is considered by the World Health Organization as one of the biggest public health security problems in the 21st century. The key to solve this problem is to use antibiotics in a timely and reasonable manner without misuse or abuse, that is, to use antibiotics in a targeted and appropriate manner according to the types of pathogenic bacteria infected by patients, which can also provide more effective treatment for patients.

At present, the most common and effective method is to provide the basis for the rational use of antibiotics in clinic through antimicrobial susceptibility test. The information includes which antibiotics the pathogenic bacteria are sensitive to and the corresponding minimum inhibitory concentration (MIC). The existing antimicrobial susceptibility testing techniques, such as broth gradient dilution method, paper diffusion method, E-test method, etc., mostly evaluate the effect of antibiotics based on whether the bacteria grow and proliferate. It usually takes a long time to cultivate (generally more than 8-16 hours) to achieve the amount of bacteria that can be distinguished by the naked eye (turbidity or bacteriostatic zone), so as to evaluate the effect of drugs. The main disadvantage is that it takes too long, Delayed guidance on rational use of antibiotics in clinical practice. Even though automated equipment is used to simplify the operation process, existing equipment, such as Vitek, BD Phoenix, Microscan Walk Away, etc., take the bacterial turbidity as the detection indicator. Although the accuracy of MIC given by the instrument has been improved, it is still limited by the longer incubation time required for bacterial division and proliferation (generally 8-24 hours) [Reference 1]. Moreover, there is a problem with these detection methods based on cell growth and proliferation, that is, the bacteria at the measured MIC concentration may be in a non-growing but metabolically active (NGMA) state, and taking this as the basis for administration may lead to recurrence of disease in later period [Reference 2] and repeated administration. In clinical practice, it is of great significance to make an accurate diagnosis in the shortest possible time and quickly treat symptomatically, whether for solving the problem of bacterial resistance or for patients, especially critically ill patients.

In view of the time-consuming problem of existing antimicrobial susceptibility test methods, emerging rapid antimicrobial susceptibility test detection technologies are also emerging, such as microfluidic based bacterial microscopic imaging technology, RNA detection method, atomic force microscope cantilever method, and Raman signal detection based on bacterial metabolism. The detection mechanisms of these methods are different, generally including: bacterial growth and proliferation, morphological changes, transcriptome changes and metabolic activity detection. With various instruments and equipment, the antimicrobial susceptibility test can be completed within 2-8 hours, to judge the bacterial sensitivity to antibiotics, and even to give a quantitative MIC. However, these methods still have a lot of shortcomings. For example, most microfluidic based bacterial microscopic imaging technologies can directly observe the growth, proliferation or morphological changes of bacteria under the action of antibiotics, which is a visual detection method and more intuitive. In addition, microfluidic technology can greatly reduce the number of samples and reagents used for detection, but microfluidic technology has not yet been popularized. The technical threshold for judging by microscopic imaging is high, and it is difficult to popularize, and the equipment cost is high, Moreover, based on the detection mechanism of bacterial growth and proliferation or morphological change, it is impossible to identify the bacteria in the non-growing but with metabolic activity (NGMA) state, which is easy to cause wrong judgment [References 3, 4, 5]. The RNA detection method judges the sensitivity of bacteria to drugs by detecting the changes in the transcripts of bacteria under the action of antibiotics. In the early stage, this method requires a large number of experiments to accumulate data and establish a database, which is time-consuming, laborious, and costly in the early stage. In addition, this method can only judge whether bacteria are sensitive to antibiotics, but cannot obtain MIC quantitatively [References 6 and 7]. Although the atomic force microscope cantilever method judges the metabolic activity of bacteria by microscopic observation and monitoring the movement of bacteria under the action of antibiotics (detecting the metabolic activity of bacteria can effectively identify the bacteria in the state of non-growing but with metabolic activity (NGMA), which is more accurate, this method is greatly affected by various factors (such as flowing liquid, number of bacteria, etc.) during detection and cannot accurately reflect the bacterial activity, In addition, the instruments and equipment are extremely complex, with high technical requirements for operation and low detection flux [Reference 8]. The method based on Raman signal also judges the effect of antibiotics by detecting bacterial metabolic activity. This method is simple in operation and short in measurement time, but it still has weak Raman signal, inaccurate MIC detection of some antibiotics, large interference from background such as sample purity, low signal to noise ratio, and poor compatibility with existing instruments (not as common as enzyme labeling instrument, flow cytometry, etc.) The price is relatively high [References 9, 10, 11].

SUMMARY OF THE INVENTION

The invention provides an evaluation method of bacterial metabolic activity based on fluorescent D-type amino acid metabolic marker, an antimicrobial susceptibility test method and a kit thereof, which are fast, simple, sensitive, accurate and intuitive, and have good compatibility with existing instruments.

On one hand, the invention relates to a method for evaluating the bacterial metabolic activity based on fluorescent D-type amino acid metabolic markers, which uses fluorescent D-type amino acid metabolic markers to metabolic labeling the bacteria to be tested, so as to evaluate the bacterial metabolic activity in the growth process according to its fluorescence intensity or fluorescence intensity change; Preferably, the specific step includes adding a fluorescent D-type amino acid metabolic marker to the bacteria to be tested for culture to label the bacteria to be tested.

On the other hand, the invention relates to an antibacterial susceptibility test method based on fluorescent D-type amino acid metabolic markers, which uses fluorescent D-type amino acid metabolic markers and antibiotic solutions to co culture bacterial solution or sample solution to be tested, to detect and obtain fluorescent marker signal intensity related to bacterial growth rate and metabolic activity and/or detect the change of fluorescent signal in real time, to evaluate bacterial metabolic activity in the process of bacterial growth; Preferably, the fluorescence signal intensity is analyzed to obtain the minimum inhibitory concentration of the antibiosis to be tested, so as to obtain the antibacterial results.

The invention also relates to a kit for the evaluation of bacterial metabolic activity and/or the detection of antimicrobial susceptibility test, which comprises a fluorescent D-type amino acid metabolic marker, and/or buffer solution, diluent or carrier, or a culture plate, or culture dish.

DESCRIPTION OF ATTACHED DRAWINGS

FIG. 1 is the structural diagram of D-type fluorescent probe with fluorescent group in the embodiment of the invention;

FIG. 2 shows the correlation data between the bacterial metabolic activity and the labeling intensity of FDAA in the embodiment of the invention; a is the data of fluorescence labeling intensity related to the metabolic activity of *Escherichia coli, Bacillus subtilis, Salmonella* and *Bacillus licheniformis* under different temperature gradients; b is the fluorescence labeling intensity data related to the metabolic activity of *Bacillus licheniformis* and *Escherichia coli* at different times. The blue curve (solid circle) is the growth rate of bacteria, which can indicate the metabolic activity of bacteria; The red curve (solid triangle) is the fluorescence intensity of the labeled bacteria; The black curve (bar) is the growth curve of bacteria. The red curve is in good agreement with the blue curve, and the fluorescence intensity of the labeled bacteria is consistent with the growth rate of bacteria, indicating that the fluorescence intensity of FDAA labeled bacteria can represent the metabolic activity of bacteria;

FIG. 27 shows the drug sensitivity test of levofloxacin, tigecycline, imipenem, amikacin and polymyxin B against *E. coli, Pseudomonas aeruginosa* (*P. aeruginosa*), *Acinetobacter baumannii* (*A. baumannii*) and *Klebsiella pneumoniae* (*K. pneumoniae*) in the specific embodiment of the application by using the fluorescent D-type amino acid metabolic marker detection method (FaAST) and VITEK.

FIG. 28 shows that in the specific embodiment of the application, fluorescent D-type amino acid metabolic marker detection method (FaAST) and VITEK are used for the drug sensitivity test of levofloxacin, vancomycin, teicoplanin, linezolid and erythromycin against *Staphylococcus aureus* and *E. faecium*.

FIG. 29 shows that in the specific embodiment of the application, the fluorescent D-type amino acid metabolic marker detection method (FaAST) and VITEK are used for the drug sensitivity test of cephalosporin antibiotics, cefepime, cefuroxime axetil, and SCF against *E. coli, P. aeruginosa, A. baumannii*, and *K. pneumoniae*, respectively.

FIG. 30 shows that in the specific embodiment of the application, fluorescent D-type amino acid metabolic marker detection method (FaAST) and VITEK are used for oxacillin drug sensitivity detection test against *Staphylococcus aureus*.

EMBODIMENTS

Figure 1:
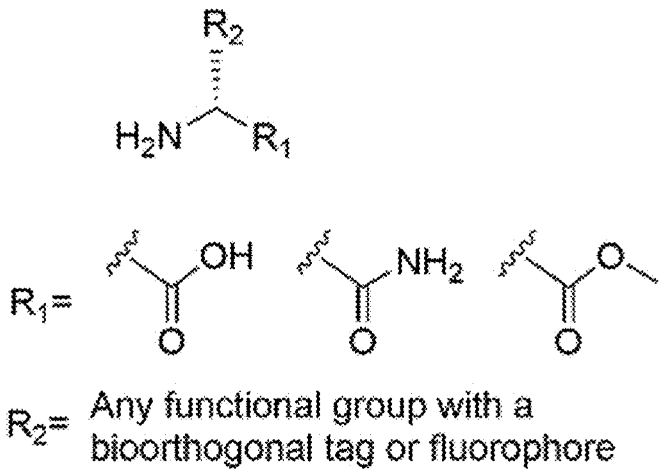

With reference to the following detailed description and exemplary embodiments, it should be understood that this application is not limited to the details or methods described in the description and shown in the drawings.

The method for evaluating bacterial metabolic activity of the invention is based on labeling bacteria with fluorescent D-type amino acid metabolic markers. Among them, D-amino acid (DAA), especially D-alanine, is a special amino acid at the end of the pentapeptide structure in bacterial peptidoglycans. At this position, bacteria will cross link with adjacent peptide segments through the peptide binding proteins (PBPs) or the transpeptidase domain in other enzymes during the synthesis and metabolism of peptidoglycans Hydrolysis (removing the terminal D-alanine) or replacement (with other D-type amino acids (DAA) in the surrounding environment) and other modifications [Reference 12]. Some penicillin binding proteins have a high tolerance to the modified groups on the D-alanine side chain. Using this feature, DAA probes with various fluorescent groups on the side chain can be connected to the bacterial peptidoglycan structure by metabolic labeling [Reference 13]. Peptidoglycan structure widely exists in all kinds of bacteria, so it can label all kinds of common bacteria; At the same time, the high cycle speed of peptidoglycan makes the labeling of DAA probe fast and strong. In the invention, if the bacteria bind more FDAA, the stronger the fluorescence signal is, indicating the stronger the metabolic activity of the bacteria. Therefore, the bacterial metabolic activity in the growth process can be evaluated according to its fluorescence intensity or the change of fluorescence intensity. The change of fluorescence intensity can be caused by the influence of the length of culture time, temperature, culture medium, the presence of growth promoting agents or bacteriostatic agents (such as antibiotics) on bacterial metabolic activity.

Fluorescent D-type amino acid metabolic marker can be a covalently modified D-type amino acid with fluorescent group or its derivatives; In the specific embodiment of the application, the fluorescent D-type amino acid metabolic marker comes from D-type alanine or its derivatives, and its structural formula is as follows (as shown in FIG. 1),

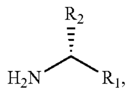

Wherein, R1 is selected from

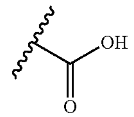

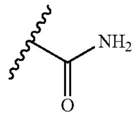

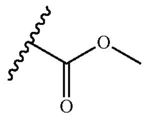

R2 is a fluorescent group. For example, in the specific embodiment of the invention, D-type alanine fluorescent probe is used. For example, fluorescent D-type amino acid metabolic markers are tetramethyl rhodamine (TRMRA) D-type amino acid fluorescent probe, D-type amino acid fluorescent probe with carboxyl fluorescein (FAM), D-type amino acid fluorescent probe with Cy5, or D-type amino acid fluorescent probe shown in the following chemical formula (hereinafter referred to as DAA-Cy5-2 probe):

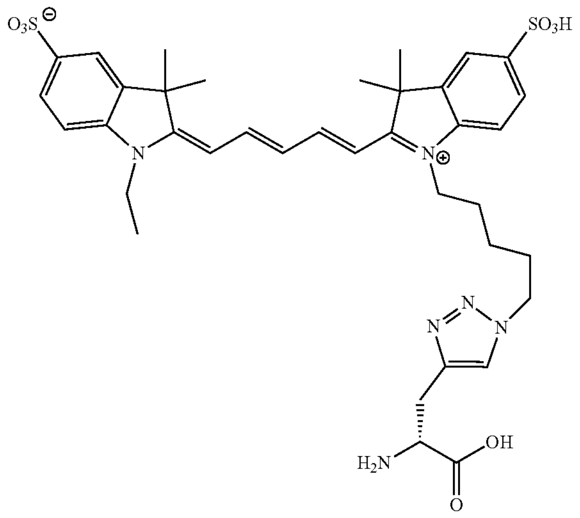

or D-type amino acid fluorescent probe (hereinafter referred to as DAA-Tetra) as shown in the following chemical formula:

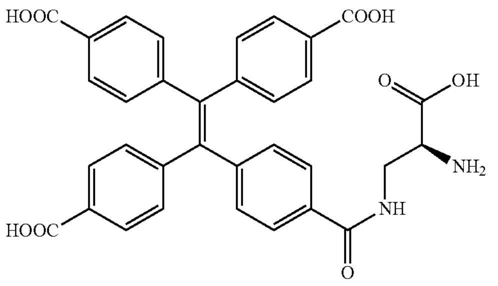 [SMILES: N[C@@H](CNC(=O)c1ccc(C(=C(c2ccc(C(=O)O)cc2)c2ccc(C(=O)O)cc2)c2ccc(C(=O)O)cc2)cc1)C(=O)O]

Figure 2A:
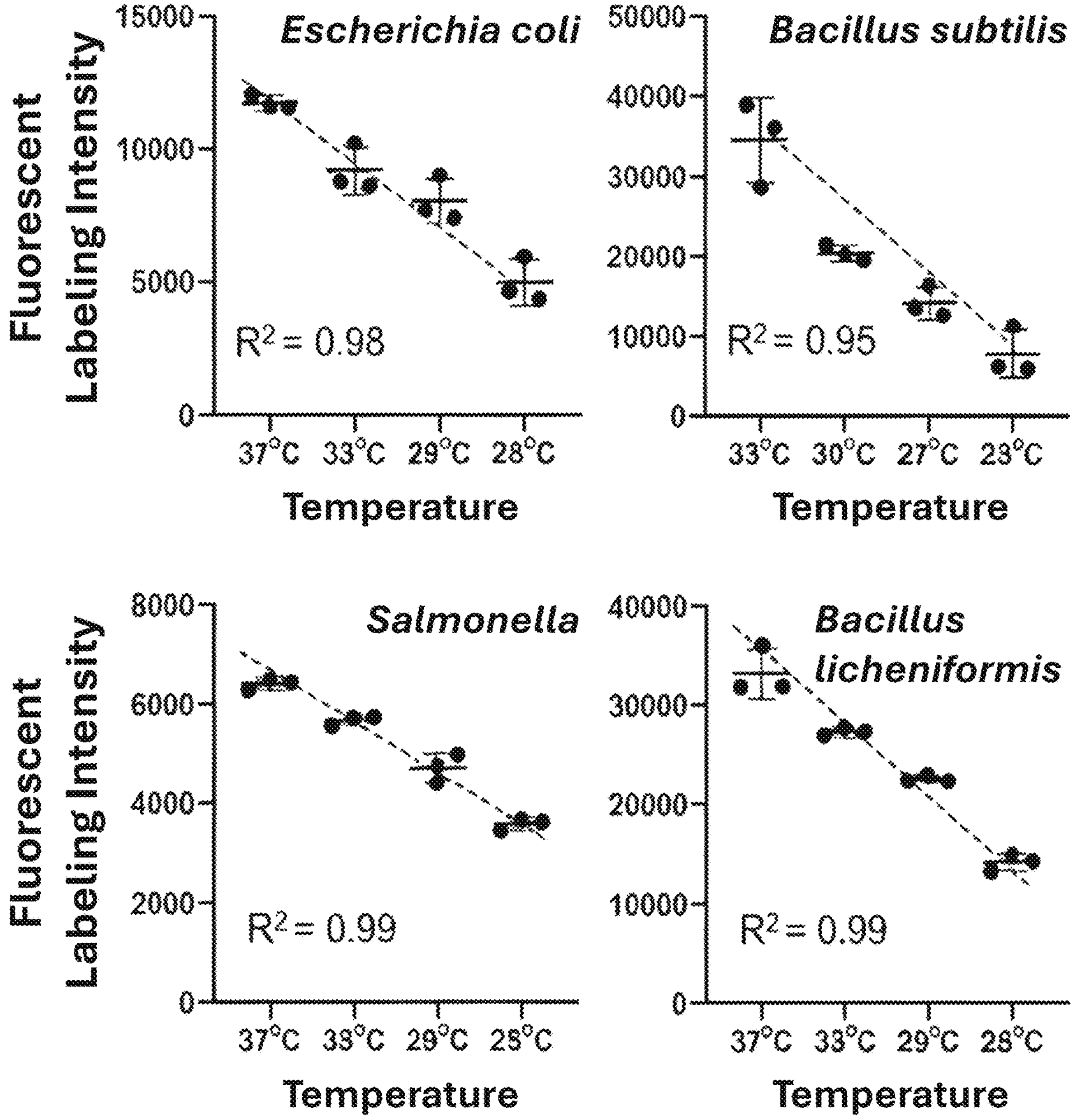
Figure 2B:
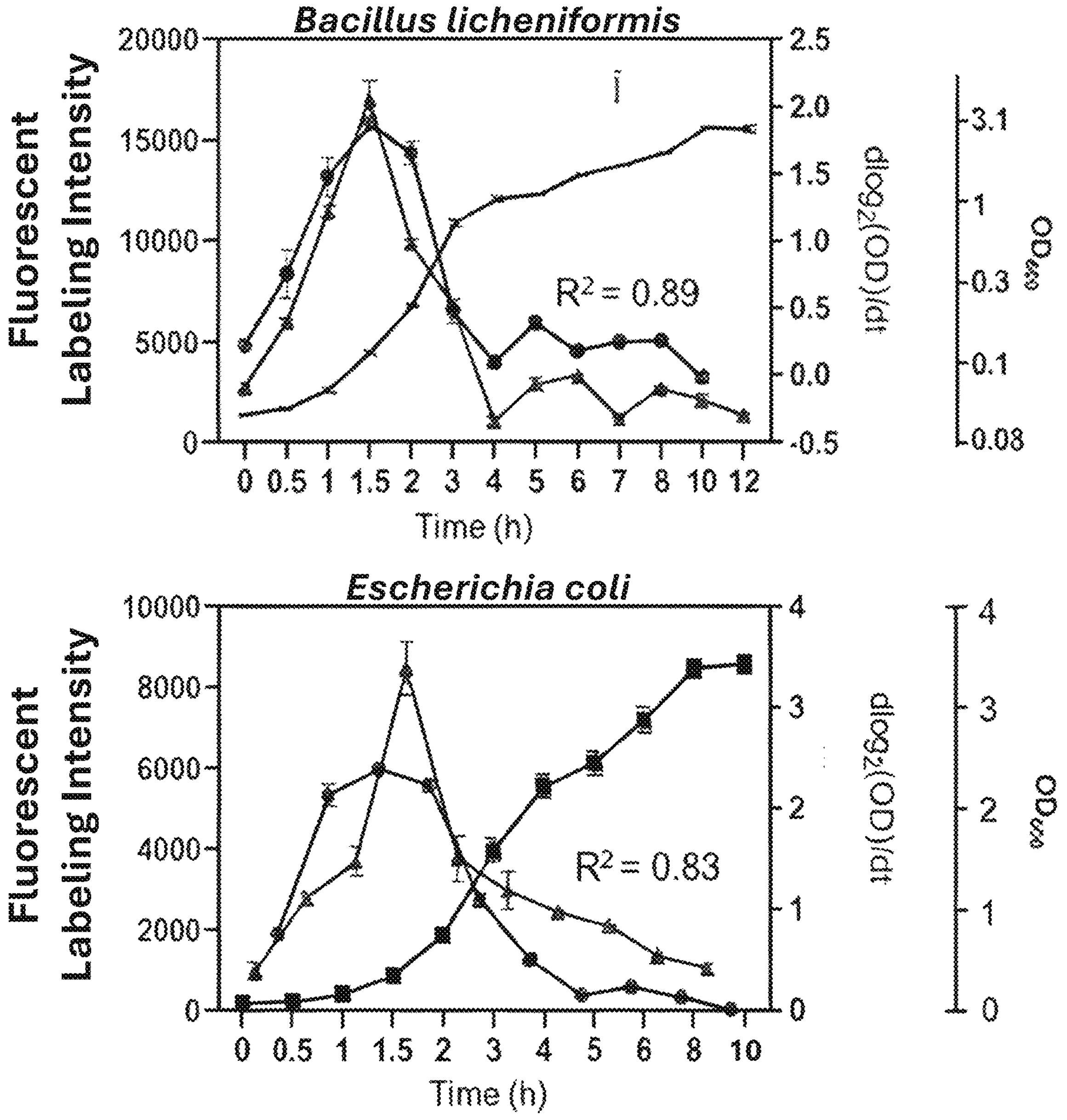

In the specific embodiment of the invention, fluorescent D-type amino acid metabolic markers are added to the bacteria to be tested and cultured to label the bacteria to be tested, such as *Escherichia coli, Bacillus subtilis, Salmonella, Bacillus licheniformis, P. aeruginosa, A. baumannii* and *K. pneumoniae*. As shown in FIG. 2-*a*, under different temperatures, *Escherichia coli, Bacillus subtilis, Salmonella*, and *Bacillus licheniformis* have different metabolic activities. The metabolic activity at 37° C. is higher than that at 33° C., 29° C. and 25° C., and the fluorescence labeling intensity is correspondingly higher than that at other temperatures, and is positively related to the metabolic activity caused by temperature. As shown in FIG. 2-*b*, the fluorescent labeling intensity of bacteria is positively correlated with the growth rate of bacteria, that is, with the change of bacterial growth and reproduction rate, the fluorescent labeling intensity also changes, reflecting that fluorescent D-type amino acid metabolic markers will be labeled on bacterial cells during bacterial growth and metabolism, indicating that it is feasible to label bacterial metabolic activity with fluorescent D-type amino acid probes, which also has high accuracy and sensitivity.

When a strain is sensitive to an antibiotic, its metabolic activity will be correspondingly inhibited, and its growth rate will also be inhibited, thus its FDAA labeling intensity will be correspondingly reduced compared with that of bacteria without antibiotics. If a strain is resistant to an antibiotic, its ability to inhibit metabolic activity will be weakened, and its FDAA labeling intensity will not be affected compared with that of the bacteria without antibiotics. The invention relates to an antibacterial susceptibility test method for D-type amino acid metabolic markers, which judges the antibacterial effect and/or bacterial resistance of antibiotics by using fluorescent D-type amino acid metabolic markers to evaluate bacterial metabolic activity, and uses fluorescent D-type amino acid metabolic markers to label bacteria, which can detect the fluorescence intensity after mixed incubation with antibiotic solution, The minimum inhibitory concentration of antibiotics was obtained according to the fluorescence signal intensity. In the specific implementation mode of the invention, the currently known fluorescence signal detection equipment or device can be used, for example, the flow cytometry (FCM) is a mature technology for rapid, sensitive and accurate multi parameter quantitative analysis and sorting of cells or biological particles in a fast flowing state using the flow cytometer. The fluorescent dye on the cell or cell is excited by the laser and emits fluorescence. The fluorescence signal is detected by the detector and converted into a digital signal that can be recognized by the computer through photoelectric conversion. The intensity of the fluorescent signal represents the number of fluorescent dyes on the bacterial cell marker.

In the specific embodiment of the application, the detection method of antimicrobial susceptibility test based on fluorescent D-amino acid metabolic marker includes the following steps: mixed culture of bacterial solution and antibiotic solution at a certain concentration and adding fluorescent D-amino acid metabolic marker, detection of the fluorescence intensity of the sample (after a period of time) and/or real-time detection of its fluorescence signal. In a specific embodiment of the application, the bacteria enter the (logarithmic) growth period by mixed incubation with antibiotic solution. In some specific embodiments of the invention, broth culture medium is used to prepare uniform bacterial solution, for example, Cation-Adjusted Mueller Hinton Broth (CAMHB) culture medium is used, and the concentration of bacterial solution can optionally be $OD_{600}$=0.2. In some specific embodiments, the antibiotic solution adopts different concentrations, such as setting gradient concentration, such as 0 μg/mL. 16 μg/mL. 32 μg/mL. 64 μg/mL. 128 μg/mL. 256 μg/ml. 512 μg/mL. 1024 μg/mL; 0 μg/mL. 2 μg/ml. 4 μg/mL. 8 μg/mL. 16 μg/ml. 32 μg/ml. 64 μG/mL and/or 128 μg/mL; 0 μg/mL. 0.0625 μg/mL. 0.125 μg/ml. 0.25 μg/mL. 0.5 μg/mL. 1 mg/ml. 2 μg/ml. 4 μG/mL and/or 8 μg/mL. In some specific embodiments, the incubation time is to enable bacteria to enter their growth period, such as 1-3 hours, more preferably 2 hours. In some specific embodiments of the application, the fluorescent D-type amino acid probe is Cy5-DAA probe, and the concentration used can label bacteria, for example, the final concentration of the probe is 0.01-5 mM, 0.1-1 mM, or 0.5 mM.

In the specific embodiment of the invention, the detection method of antimicrobial susceptibility test based on fluorescent D-amino acid metabolic marker can be used for gram-positive bacteria and gram-negative bacteria, for example, gram-negative bacteria include, but are not limited to, *Klebsiella pneumoniae, Pseudomonas aeruginosa, Acinetobacter baumannii, Haemophilus influenzae, Enterobacter aerogenes, Serratia marcescens, Klebsiella acidogenes*, and *Escherichia coli* (*E. coli*). Gram positive bacteria include but are not limited to *Staphylococcus aureus, Streptococcus pneumoniae, Enterococcus faecalis, Staphylococcus epidermidis, Staphylococcus capitis*, and *Streptococcus* pharyngitis. For example, *Staphylococcus aureus* is a high-level OX resistant strain ST5, a low-level OX resistant strain ST59, and an OX sensitive strain ST398; *Escherichia coli* was drug resistant strain 1113 and sensitive strain 1146. Antibiotics that can be targeted by the invention, for example, include but are not limited to penicillins, cephalosporins, mercaptopenilenes, aminoglycosides, tetracyclines, amide alcohols, macrolides, glycopeptides, sulfonamides, quinolones, and nitroimidazoles. The antibacterial susceptibility test method of fluorescent D-amino acid metabolic marker involved in this application can be used to detect the influence of antibiotics with different action mechanisms on different bacterial metabolic activities at sub inhibitory concentrations, the detection of bacterial metabolic activities under low concentration antibiotic treatment, detection of metabolic activity of antibiotics on bacteria in different growth stages, and the detection of MIC changes of bacteria to corresponding antibiotics after long-term low concentration antibiotic action.

Figure 26:
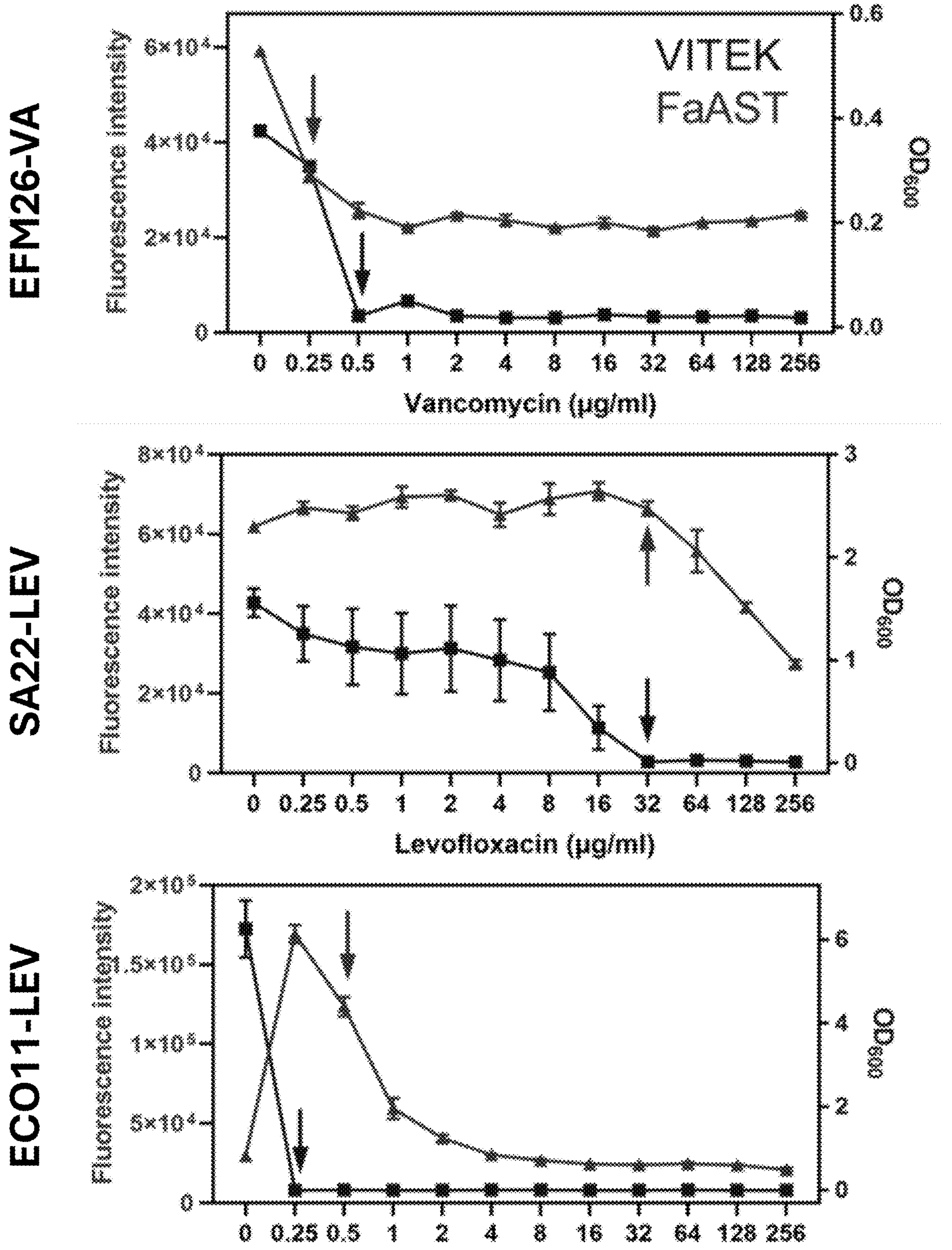
FIG. 26 shows that in the specific embodiment of the application, fluorescent D-type amino acid metabolic marker detection method (FaAST) and VITEK are used to detect the drug sensitivity of levofloxacin (LEV) and vancomycin (VA) to EFM26 (*Enterococcus faecium*), SA22 (*Staphylococcus aureus*) and ECO11 (*Escherichia coli*) respectively.

The present invention relates to the use of fluorescent D-type amino acid metabolic markers for evaluating bacterial metabolic activity and/or antimicrobial susceptibility testing. As shown in FIG. 26, according to the specific operation steps of the following embodiments, levofloxacin (LEV) and vancomycin (VA) were used to treat EFM26 (*Enterococcus faecium*), SA22 (*Staphylococcus aureus*) and ECO11 (*Escherichia coli*) respectively, and VITEK and fluorescent D-type amino acid metabolite marker (FaAST) were used to calculate and obtain the antibiotic MIC (minimum inhibitory concentration), as shown in FIG. 26, The result obtained by FaAST is highly consistent with that obtained by the traditional VITEK method. The FaAST method is used in the test of gram-negative bacteria. As shown in FIG. 27, levofloxacin, tegacyclin, imipenem, amikacin and polymyxin B are used for the drug sensitivity test against *E. coli, P. aeruginosa, A. baumannii* and *K. pneumoniae*. The strains involved in *E. coli* are Ec11, Ec13 and Ec ATCC25922, *P. aeruginosa* involves Pa2, Pa3 and Pa ATCC 27853, *A. baumannii* involves Ab16 and Ab19, and *K. pneumoniae* involves Kp6 and Kp9. As shown in FIG. 28, levofloxacin, vancomycin, teicoplanin, linezolid, and erythromycin were used to carry out the Gram positive bacteria susceptibility test against *Staphylococcus aureus* and *Enterococcus faecium* (*E. faecium*). *Staphylococcus aureus* (*S. aureus*) involved strains Sa22, Sa23, Sa ATCC 29213, and *E. faecium* involved strains Ef26, Ef28, Ef ATCC 29212; According to FIG. 27 and FIG. 28, the FaAST method and the traditional VITEK method showed high consistency in the detection results of drug-resistant bacteria, for example, levofloxacin against Ec13, imipenem against Ec13, polymyxin B against Ec13, imipenem against Pa3, levofloxacin against Ab16, imipenem against Ab16, amikacin against Ab16, levofloxacin against Kp9, imipenem against Kp9, amikacin against Kp9, etc; Levofloxacin against Sa22, levofloxacin against Ef26 and Ef28, linezolid against Sa23, and erythromycin against Ef28. In another embodiment of the invention, referring to the cephalosporins antibiotic test shown in FIG. 29, cefepime, cefuroxime axetil and SCF respectively target against *E. coli, P. aeruginosa, A. baumannii* and *K. pneumoniae* in the drug sensitivity test. The strains of *E. coli* are Ec11, Ec13 and Ec ATCC25922, and the strains of *P. aeruginosa* are Pa2, Pa3 Pa ATCC 27853, *Acinetobacter baumannii* related bacteria are Ab16 and Ab19, and *K. pneumoniae* related bacteria are Kp6 and Kp9. The FaAST and VITEK methods of the invention show high consistency in the detection results of drug resistant bacteria. In another embodiment of the application, oxacillin is used to detect the drug sensitivity of *Staphylococcus aureus*, as shown in FIG. 30. *Staphylococcus aureus* involves strains Sa22, Sa23, Sa24, Sa25, Sa31, Sa5, Sa59, Sa398, Sa ATCC43380, Sa ATCC29213, etc. The results of FaAST are highly consistent with those obtained by BMD method.

In view of the analysis results of the accuracy of the FaAST method in this application, 30 standard strains and clinically isolated strains were used to test ten typical antibiotics respectively. In terms of classification deviation and accuracy, the accuracy of the FaAST results in this application was significantly higher than the accuracy standard specified by FDA, and the structure is as follows:

| Classification deviation and accuracy | Accuracy standards specified by FDA | Accuracy of FaAST results |
|---|---|---|
| Minor deviation | <10% | 0.96% |
| Large deviation | <3% | 1.49% |
| Major deviation | <1.5% | 0% |
| Classification accuracy | >90% | 98.08% |

In the specific embodiment of the invention, the kit for bacterial metabolic activity evaluation and/or antimicrobial susceptibility test comprises fluorescent D-amino acid metabolic markers, and/or buffer solution, diluent or carrier, or culture plate, or culture dish.

The technical scheme of the invention is further described below in combination with specific embodiments.

Example 1

The effect of oxacillin (OX), vancomycin (VA) and erythromycin (E) on the high level OX resistant strain ST5, low level OX resistant strain ST59 and OX sensitive strain ST398 of gram-positive *Staphylococcus aureus* (*S. aureus*) was tested by using FDAA metabolic labeling method.

Figure 3:
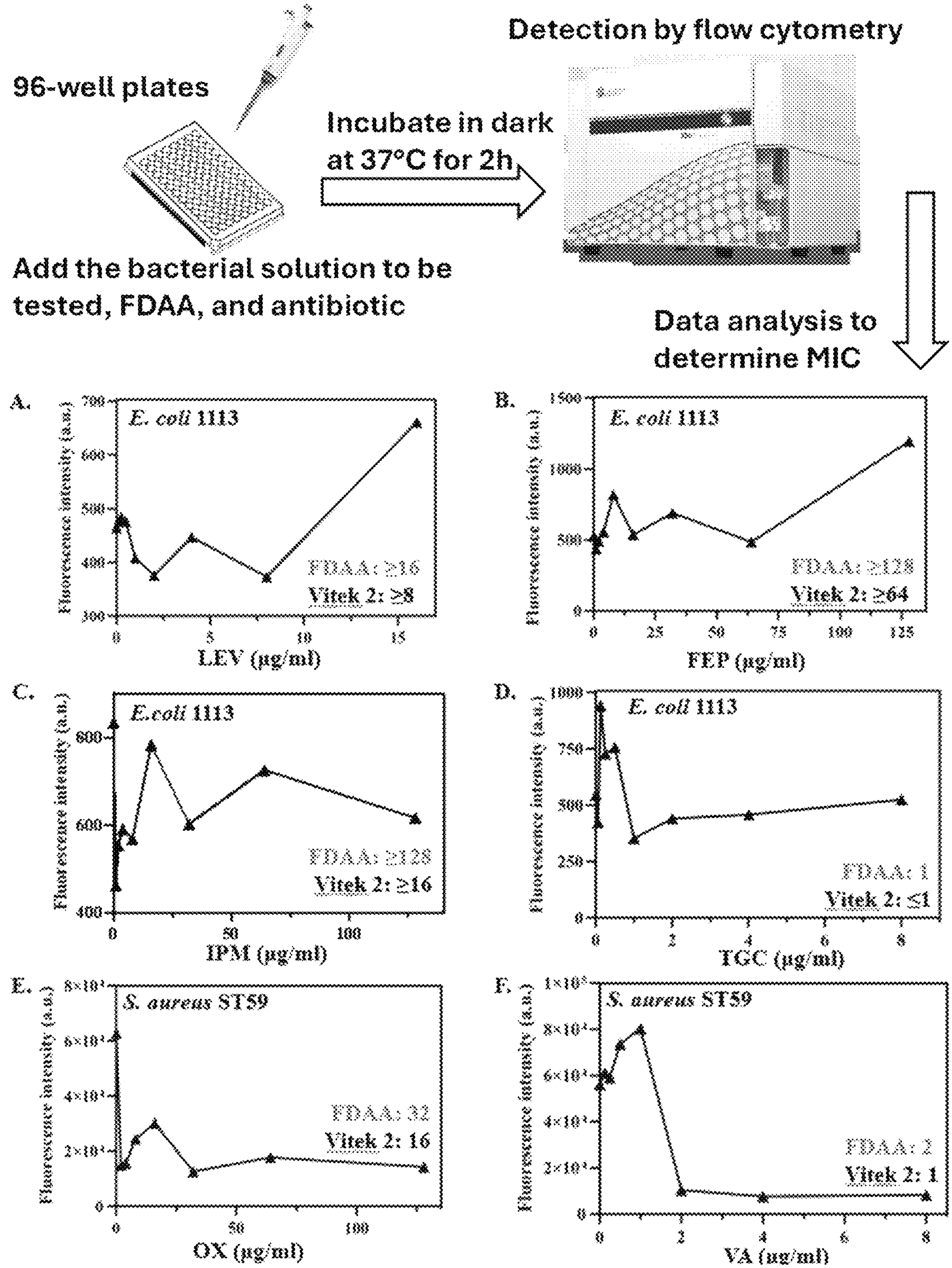
FIG. 3 is the flow chart of the rapid detection method of antimicrobial susceptibility test based on FDAA metabolic markers.
Figure 4:
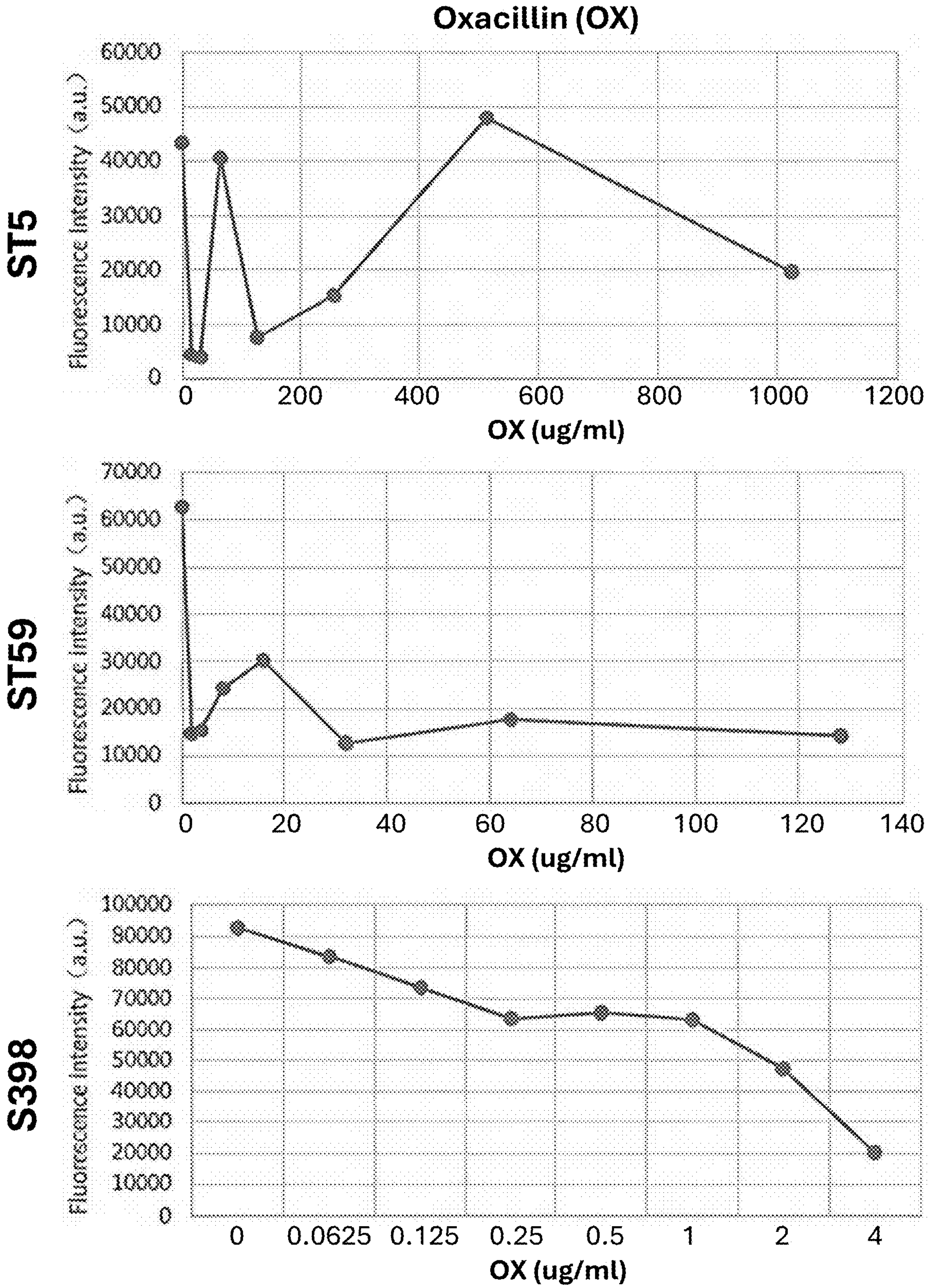
FIG. 4 shows the effect of oxacillin (OX) on high level OX resistant strain ST5, low level OX resistant strain ST59 and OX sensitive strain ST398 of gram-positive *Staphylococcus aureus* (*S. aureus*) in the specific embodiment of the application.
Figure 5:
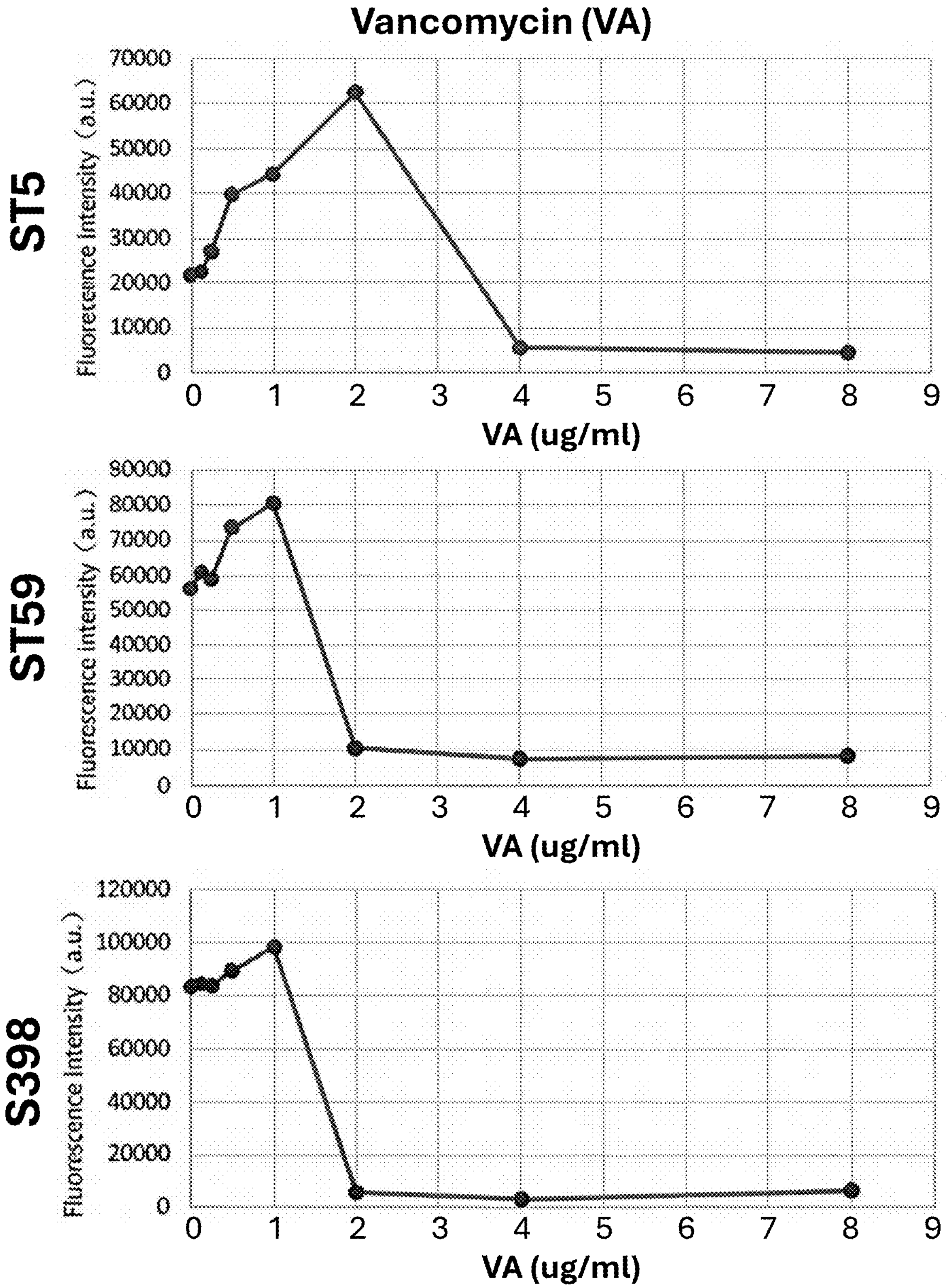
FIG. 5 shows the effect of vancomycin (VA) on high level OX resistant strain ST5, low level OX resistant strain ST59 and OX sensitive strain ST398 of gram-positive *Staphylococcus aureus* (*S. aureus*) in the specific embodiment of the application.
Figure 6:
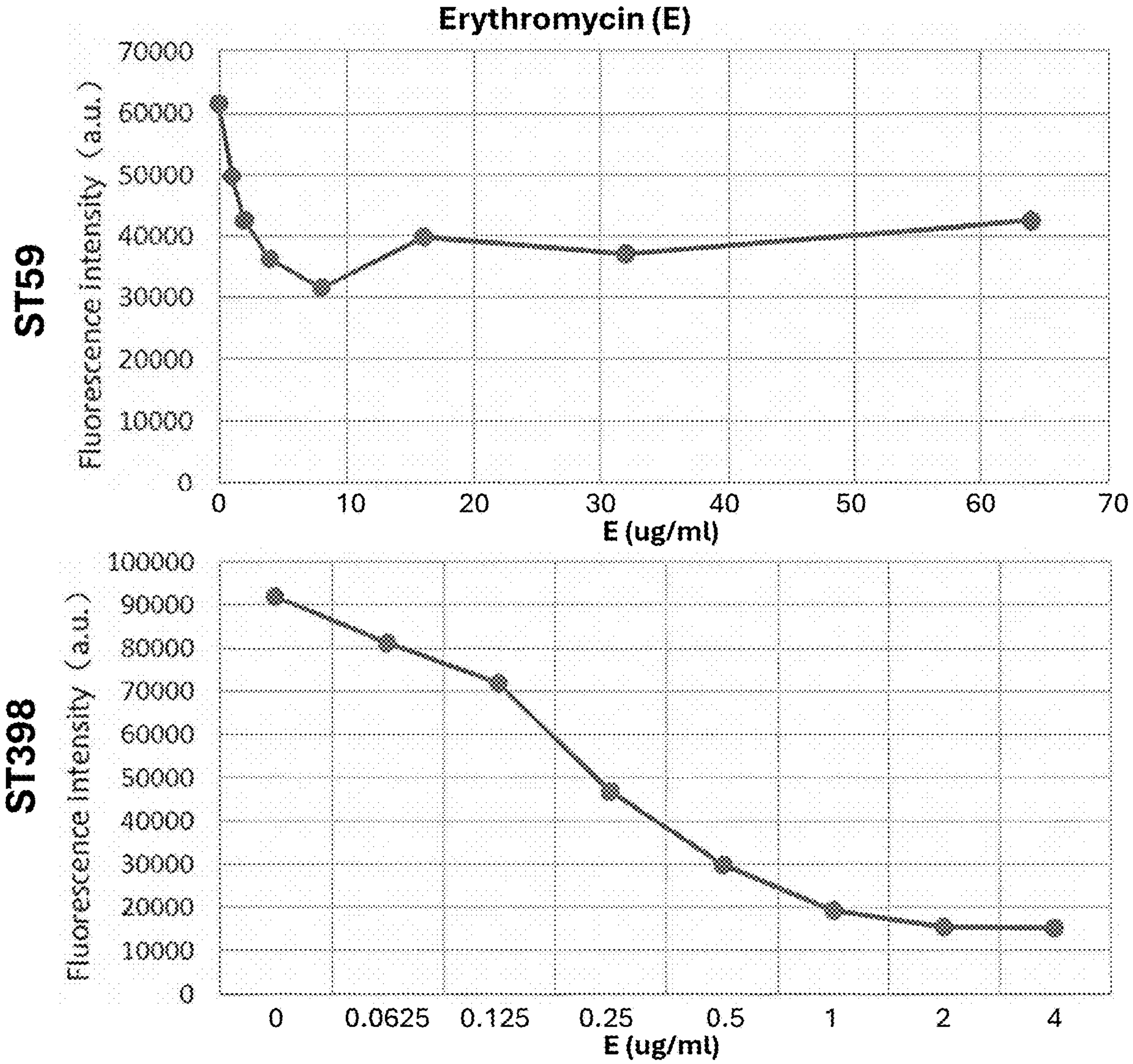
FIG. 6 shows the effect of erythromycin (E) on high level OX resistant strain ST5, low level OX resistant strain ST59 and OX sensitive strain ST398 of gram-positive *Staphylococcus aureus* (*S. aureus*) in the specific embodiment of the application.
Figure 7:
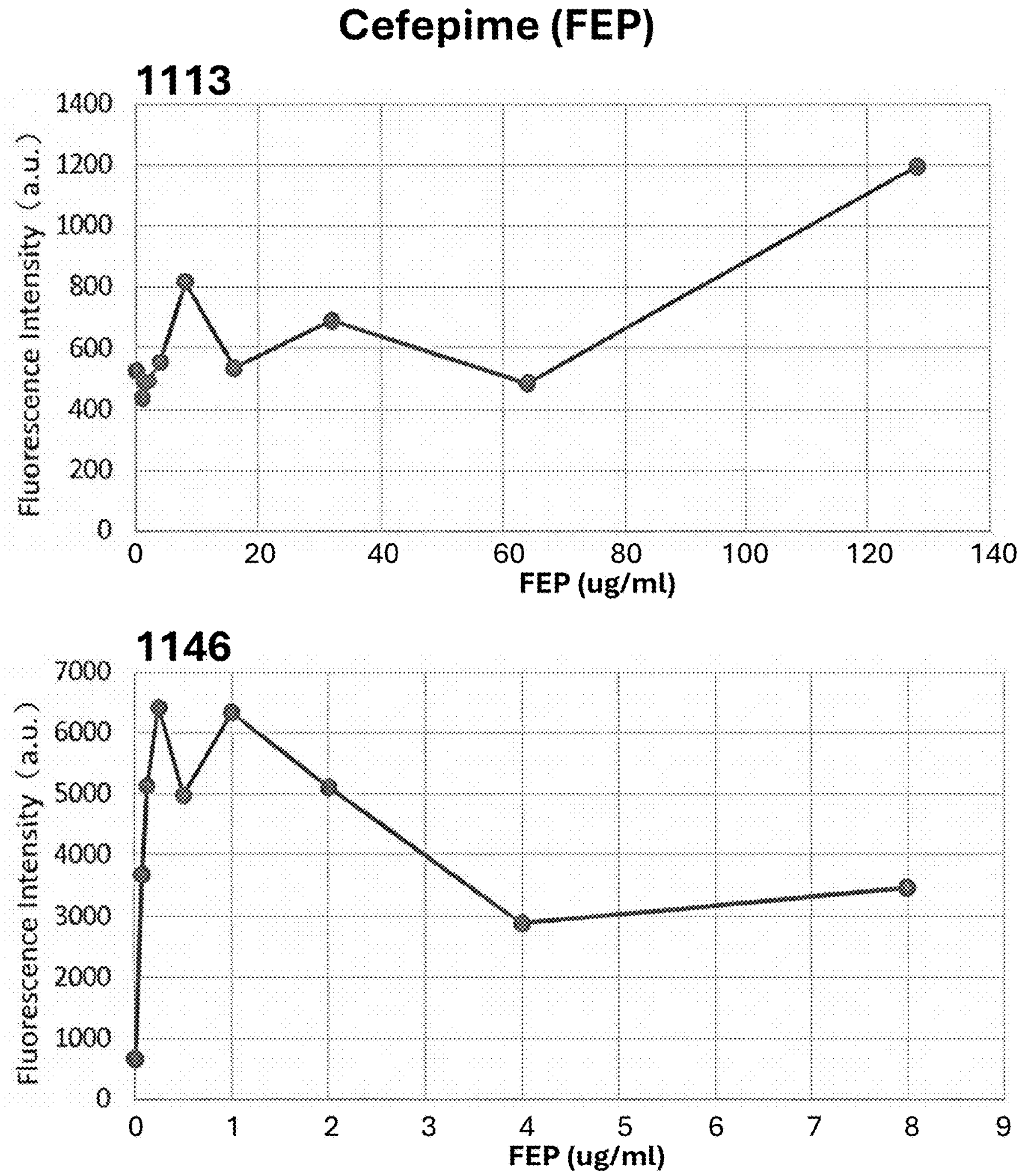
FIG. 7 shows the effect of cefepime (FEP) on resistant strain 1113 and sensitive strain 1146 of gram-negative *Escherichia coli* (*E. coli*) in the specific embodiment of the application.
Figure 8:
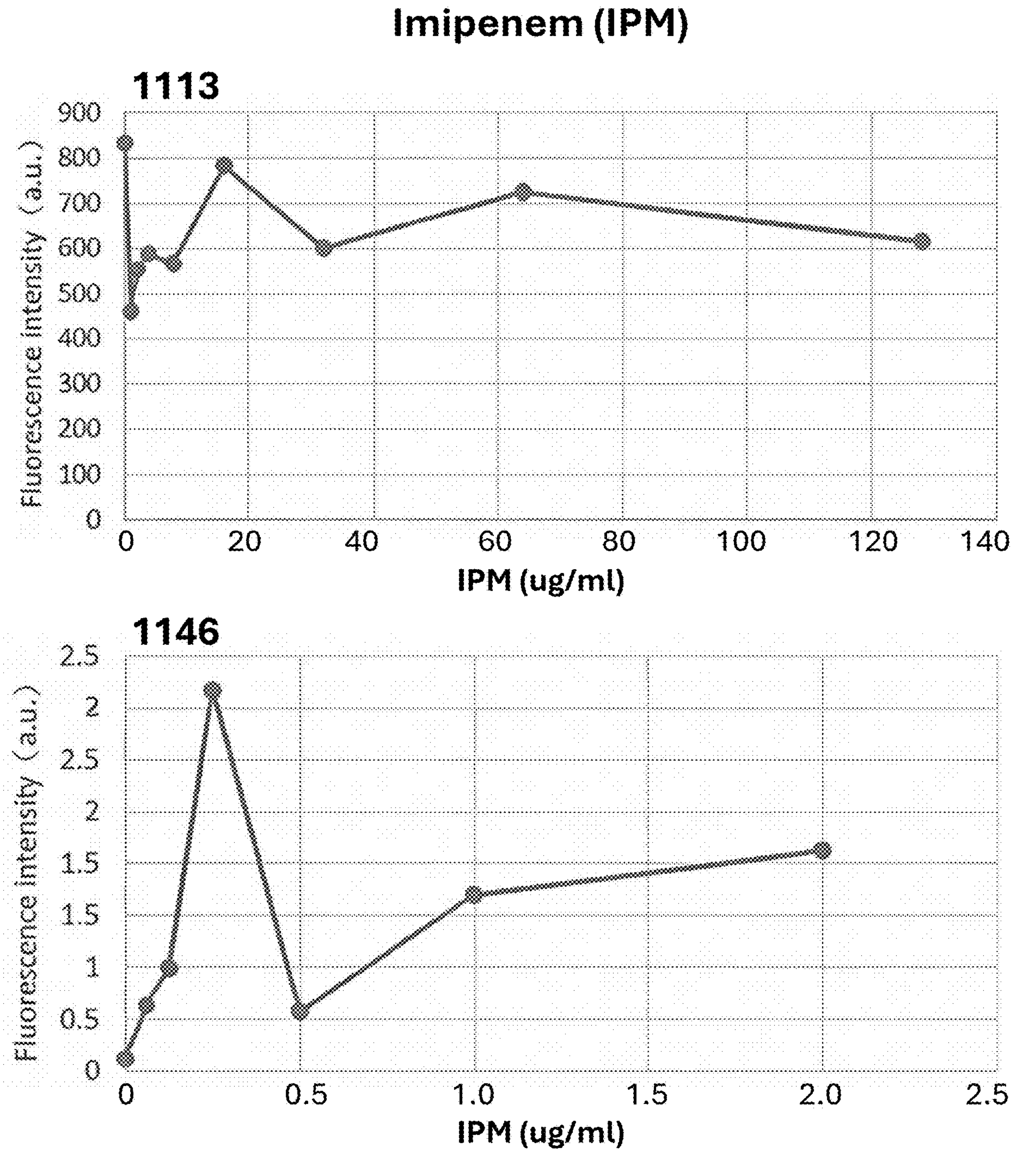
FIG. 8 shows the effect of imipenem (IPM) on resistant strain 1113 and sensitive strain 1146 of gram-negative *Escherichia coli* (*E. coli*) in the specific embodiment of the application.
Figure 9:
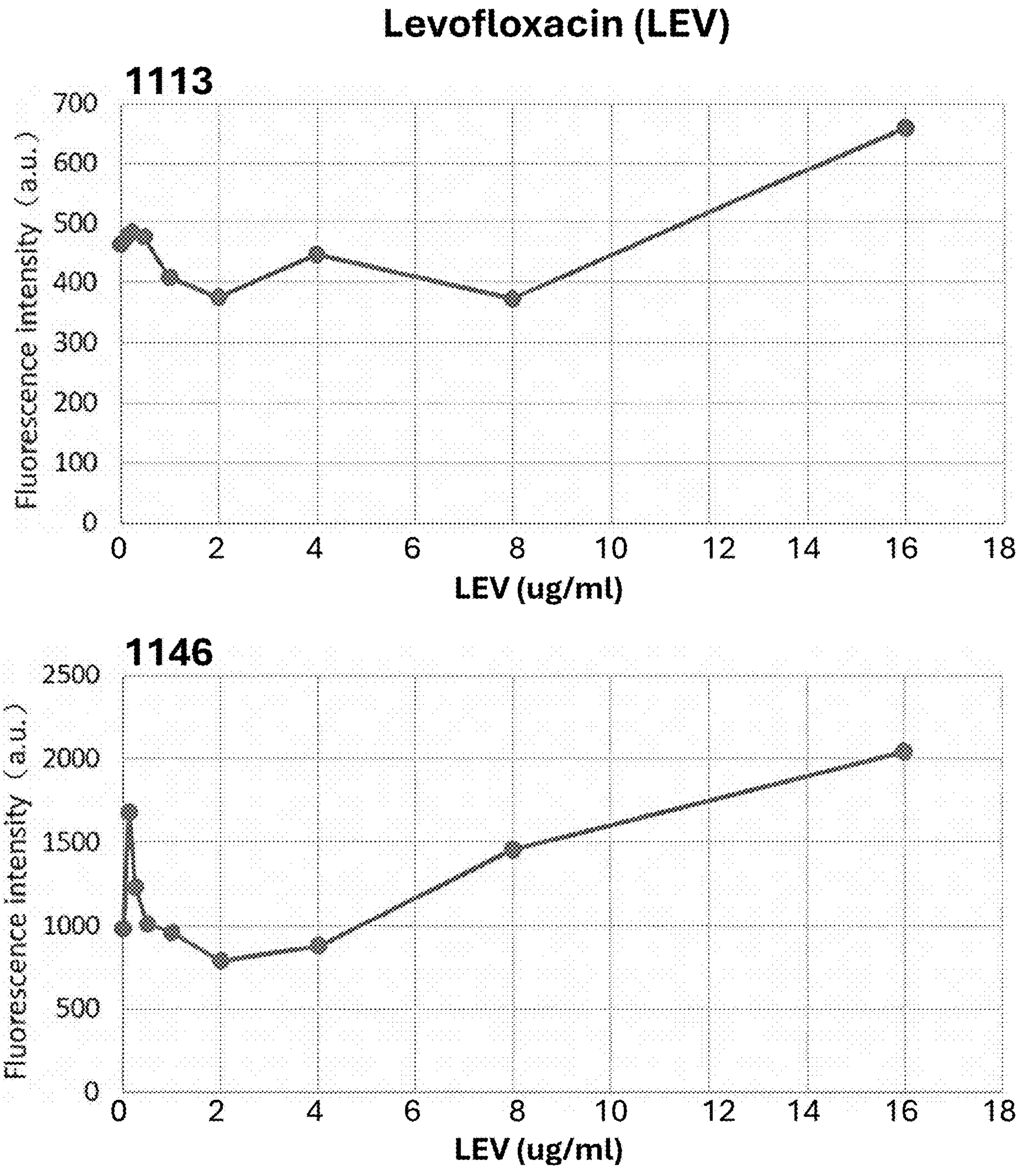
FIG. 9 shows the effect of levofloxacin (LEV) on resistant strain 1113 and sensitive strain 1146 of gram negative *Escherichia coli* (*E. coli*) in the specific embodiment of the application.
Figure 10:
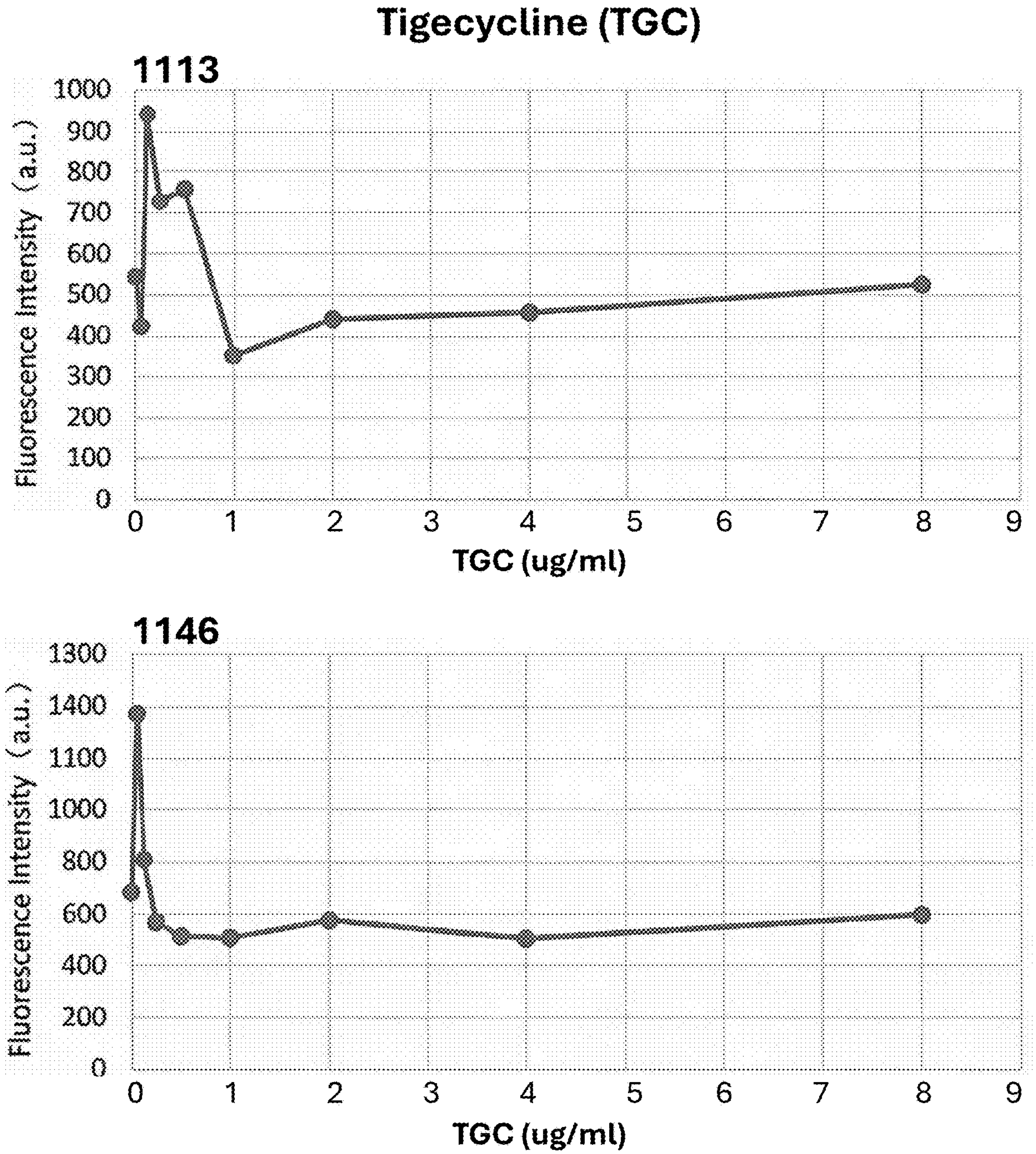
FIG. 10 shows the effect of tigecycline (TGC) on resistant strain 1113 and sensitive strain 1146 of gram negative *Escherichia coli* (*E. coli*) in the specific embodiment of the application.

As shown in FIG. 3, the flow chart of a rapid detection method for antimicrobial susceptibility test based on FDAA metabolic markers is as follows:

1. Take the colony to be tested that has been cultured overnight on the plate and fully mix it in normal saline to make a uniform bacterial solution. Dilute it into Cation-Adjusted Mueller Hinton Broth (CAMHB) culture medium to make a bacterial solution with $OD_{600}$=0.05.
2. Add 45 μl antibiotic solutions of different concentrations to 96-well plates (see Table 1 for antibiotic concentration gradient settings).
3. Add 50 μl of the bacterial solution prepared in step 1 to the 96-well plate and mix well.
4. Add 5 μl of 10 mM Cy5-DAA probe (final concentration 0.15 mM, see FIG. 1 for its structure) into each well, mix well, and cultivate in dark for 2 hours.
5. Add 200 μl After PBS solution is diluted, the fluorescence intensity of each sample is detected by flow cytometry. The flow detection results are shown in FIG. 4-5, showing the curve of the change of antibiotic concentration gradient and fluorescence intensity. The MIC (minimum inhibitory concentration) can be obtained by referring to this curve.

TABLE 1

| Antibiotic concentration gradient settings (final concentration, μg/ml) | | | |
|---|---|---|---|
| | *S. Aureus* strain | | |
| Antibiotic | ST5 | ST59 | ST398 |
| Oxacillin(OX) | 0, 16, 32, 64, 128, 256, 512, 1024 | 0, 2, 4, 8, 16, 32, 64, 128 | 0, 0.0625, 0.125, 0.25, 0.5, 1, 2, 4 |
| Vancomycin(VA) | 0, 0.125, 0.25, 0.5, 1, 2, 4, 8 | | |
| Erythromycin (E) | — | 0, 1, 2, 4, 8, 16, 32, 64 | 0, 0.0625, 0.125, 0.25, 0.5, 1, 2, 4 |

It can be seen from Table 2 below that the drug sensitivity test results of gram-positive bacteria obtained by the invention (rapid detection method of antimicrobial drug sensitivity test based on FDAA metabolic markers) are in good agreement with those obtained by Vitek 2, a commonly used clinical drug sensitivity test device.

TABLE 2

| Comparison of detection results of FDAA metabolic labeling method and clinical common drug sensitivity test equipment Vitek 2 (Gram positive bacteria) | | | | | | | | | |
|---|---|---|---|---|---|---|---|---|---|
| | MIC, FDAA (μg/ml) | MIC, Vitek 2 (μg/ml) | Sensibility | MIC, FDAA (μg/ml) | MIC, Vitek 2 (μg/ml) | Sensibility | MIC, FDAA (μg/ml) | MIC, Vitek 2 (μg/ml) | Sensibility |
| Antibiotic | *S. aureus* ST5 | | | *S. aureus* ST59 | | | *S. aureus* ST398 | | |
| OX | ≥1024 | 256 | R | 32 | 16 | R | 0.25 | ≤0.25 | S |
| VA | 4 | 1 | S | 2 | 1 | S | 2 | ≤0.5 | S |
| E | — | — | — | 8 | ≥8 | R | 0.5 | ≤0.25 | S |

Note:
S: Drug sensitive;
R: Drug resistance

Example 2

FDAA metabolic labeling method and BMD were used to detect the effect of levofloxacin, vancomycin, teicoplanin, linezolid, erythromycin and penicillin G on gram-positive *S. aureus, E. faecium* and *E. faecalis* (the other steps were the same as Example 1). Bacteria with antibiotic resistance are shown in bold in the following table.

| | Antibiotics | | | | | | |
|---|---|---|---|---|---|---|---|
| | *S. aureus* | | | | | | |
| | Sa22 | | Sa23 | | ATCC29213 | | |
| Bacteria | BMD | FaAST | BMD | FaAST | CLSI QC range | BMD | FaAST |
| Levofloxacin | **32** | **32** | 1 | 1 | 0.06-0.5 | ≤0.25 | 0.5 |
| Vancomycin | 1 | 2 | 1 | 2 | 0.5-2 | 1 | 1 |
| Teicoplanin | 0.5 | 1 | 0.5 | 1 | 0.25-1 | ≤0.25 | 0.25 |
| Linezolid | 2 | 1 | **8** | **8** | 1-4 | 2 | 2 |
| Erythromycin | — | — | — | — | — | — | — |
| Penicillin G | — | — | — | — | — | — | — |

-continued

| | Antibiotics | | | | | | |
|---|---|---|---|---|---|---|---|
| | *E. faecium* | | | | *E. faecalis* | | |
| | Ef26 | | Ef28 | | ATCC29212 | | |
| Bacteria | BMD | FaAST | BMD | FaAST | CLSI QC range | BMD | FaAST |
| Levofloxacin | ≥256 | **64** | **≥256** | **64** | 0.25-2 | 1 | 1 |
| Vancomycin | 0.5 | 0.25 | **≥256** | **32** | 1-4 | 2 | 2 |
| Teicoplanin | 0.5 | 0.25 | **16** | **32** | 0.25-1 | ≤0.25 | 0.5 |
| Linezolid | 2 | 2 | 2 | 2 | **1-4** | 1 | 2 |
| Erythromycin | ≤0.25 | ≤0.25 | **≥256** | **≥256** | **1-4** | **2** | **2** |
| Penicillin G | 64 | 32 | **≥256** | **256** | 1-4 | 2 | 4 |

Example 3

The effect of cefepime (FEP), imipenem (IPM), levofloxacin (LEV) and tigecycline (TGC) on resistant strain 1113 and sensitive strain 1146 of Gram negative *Escherichia coli* (*E. coli*) was tested by FDAA metabolic labeling method.

The specific experimental steps are as follows:

1. Take the colony to be tested that has been cultured overnight on the plate and fully mix it in normal saline to make a uniform bacterial solution. Dilute it into CAMHB medium to make a bacterial solution with $OD_{600}$=0.05.
2. Add 45 µl antibiotic solutions to be tested of different concentrations to 96-well plates (see Table 3 for antibiotic concentration gradient settings).
3. Add 50 µl of bacterial solution prepared in Step 1 to the 96-well plate and mix well.
4. 5 µl of 10 mM Cy5-DAA probe was added to each well (final concentration was 0.15 mM, and its structure was shown in FIG. 1). After mixing, the probe was incubated for 2 hours in the dark.
5. After dilution with 200 µl PBS solution, the fluorescence intensity of each sample was detected by flow cytometry. The flow detection results are shown in the attached FIG. 4-5, showing the curve of antibiotic concentration gradient and fluorescence intensity, and the MIC (minimum inhibitory concentration) is obtained by referring to this curve.

TABLE 3

| Antibiotic concentration gradient settings (final concentration, µg/mL) | | |
|---|---|---|
| | *E. coli* strains | |
| Antibiotic | 1113 | 1146 |
| FEP | 128, 64, 32, 16, 8, 4, 2, 1, 0 | 8, 4, 2, 1, 0.5, 0.25, 0.125, 0.06, |
| IPM | 128, 64, 32, 16, 8, 4, 2, 1, 0 | 8, 4, 2, 1, 0.5, 0.25, 0.125, 0.06, |
| LEV | 16, 8, 4, 2, 1, 0.5, 0.25, 0125, 0 | |
| TGC | 8, 4, 2, 1, 0.5, 0.25, 0.125, 0.06, 0 | |
| Blank control * | 0 (no probe) | 0 (no probe) |

Blank control *: No antibiotics and probes are added.

As shown in Table 4 below, the drug sensitivity test results of gram-negative bacteria obtained by the invention (rapid detection method of antimicrobial drug sensitivity test based on FDAA metabolic markers) are in good agreement with those obtained by Vitek 2, a commonly used clinical drug sensitivity test device.

TABLE 4

| Comparison of detection results of FDAA metabolic labeling method and clinical common drug sensitivity test equipment Vitek 2 (Gram negative bacteria) | | | | | | |
|---|---|---|---|---|---|---|
| | MIC, FDAA (µg/ml) | MIC, Vitek 2 (g/ml) | Sensibility | MIC, FDAA (µg/ml) | MIC, Vitek 2 (µg/ml) | Sensibility |
| Antibiotic | *E.coli* 1113 | | | *E.coli* 1146 | | |
| FEP | ≥128 | ≥64 | R | 4 | ≤1 | S |
| IPM | ≥128 | ≥16 | R | 0.5 | ≤1 | S |
| LEV | ≥16 | ≥8 | R | ≥16 | ≥8 | R |
| TGC | 1 | ≤1 | S | 0.25 | ≤0.25 | S |

Note:
S: Drug sensitive;
R: Drug resistance

Example 4

Levofloxacin, Tigecycline, Imipenem, Amikacin and Polymyxin B, Cefepime, Cefuroxime and SCF were detected by FDAA metabolic labeling and BMD for the effect on Gram-negative *Escherichia coli* (*E. coli*), *P. aeruginosa, Acinetobacter baumannii* and *K. pneumoniae* (the other steps are the same as in Example 3). Antibiotic resistant strains are shown in bold in the table below.

| | Bacteria | | | | | | | | | | |
|---|---|---|---|---|---|---|---|---|---|---|---|
| | *E. coli* | | | | | | | | | | |
| | | | | | Ec ATTC 25922 | | | *P. aeruginosa* | | | |
| | Ec11 | | Ec13 | | CLSI QC | | | Pa2 | | Pa3 | |
| Antibiotics | BMD | FaAST | BMD | FaAST | range | BMI | FaAST | BMD | FaAST | BMD | FaAST |
| Levofloxacin | ≤0.25 | 0.5 | — | — | 0.008-0.06 | ≤0.25 | <0.25 | 0.5 | 0.5 | 0.5 | 0.5 |
| Tigecycline | ≤0.25 | ≤0.25 | <0.25 | <0.25 | 0.03-0.25 | ≤0.25 | ≤0.25 | — | — | — | — |
| Imipenem | ≤0.25 | 1 | **16** | **128** | 0.06-0.25 | ≤0.25 | 1 | 1 | 1 | 32 | 32 |
| Amikacin | 4 | 8 | 2 | 1 | 0.5-4 | 1 | 2 | 2 | 0.5 | 4 | 8 |
| 16 | | | | | | | | | | | |
| Polymyxin B | 2 | 2 | b | 8 | 0.25-2 | 2 | 2 | — | — | — | — |
| Cefepime | ≤0.25 | 0.5 | >64 | >128 | 0.016-0.12 | ≤0.25 | ≤0.25 | 1 | 0.5 | 8 | 4 |
| Cefuroxime | 4 | 8 | ≥256 | ≥256 | 2-8 | 4 | 8 | — | — | — | — |
| SCF[b] | ≤0.25 | 1 | ≥256 | ≥256 | — | 0.5 | 1 | 4 | 8 | 8 | 16 |

| | Bacteria | | | | | | | | | | |
|---|---|---|---|---|---|---|---|---|---|---|---|
| | *P. aeruginosa* Pa ATCC 27853 | | | *A. baumannu* | | | | *K. pneumoniae* | | | |
| | CLSI | | | Ab16 | | Ab19 | | Kp6 | | Kp9 | |
| Antibiotics | QC | BMD | FaAST | BMD | FaAST | BMD | FaAST | BMD | FaAST | BMD | FaAST |
| Levofloxacin | 0.5-4 | 0.5 | 0.5 | **16** | **32** | ≤0.25 | 0.5 | ≤0.25 | 0.5 | **32** | **128** |
| Tigecycline | — | — | — | ≤0.25 | ≤0.25 | ≤0.25 | 0.5 | ≤0.25 | ≤0.25 | 0.5 | 0.25 |
| Imipenem | 1-4 | 2 | 1 | **32** | **64** | ≤0.25 | 1 | ≤0.25 | 1 | **128** | **256** |
| Amikacin | 1-4 | 2 | 4 | **>256** | **≥256** | 2 | 2 | 0.5 | 0.5 | **≥256** | **≥256** |
| 16 | | | | | | | | | | | |
| Polymyxin B | — | — | — | — | — | — | — | 0.5 | 1 | **16** | **32** |
| Cefepime | 0.5-4 | 2 | 2 | **128** | **64** | 1 | 1 | ≤0.25 | 0.5 | **≥256** | **≥256** |
| Cefuroxime | — | — | — | — | — | — | — | 2 | 4 | **≥256** | **≥256** |
| SCF[b] | | 4 | 4 | **64** | **≥256** | 1 | 1 | ≤0.25 | 0.5 | **≥256** | **≥256** |

Example 5

Figure 11:
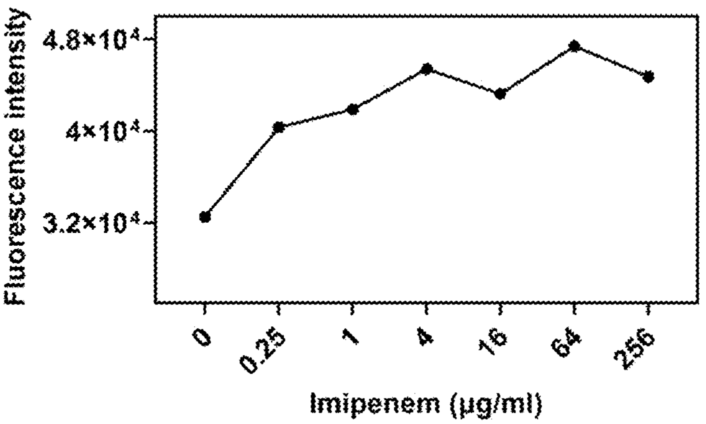
FIG. 11 shows the effect of imipenem (IPM) on bacteria contained in alveolar lavage fluid in the specific embodiment of the application.
Figure 12:
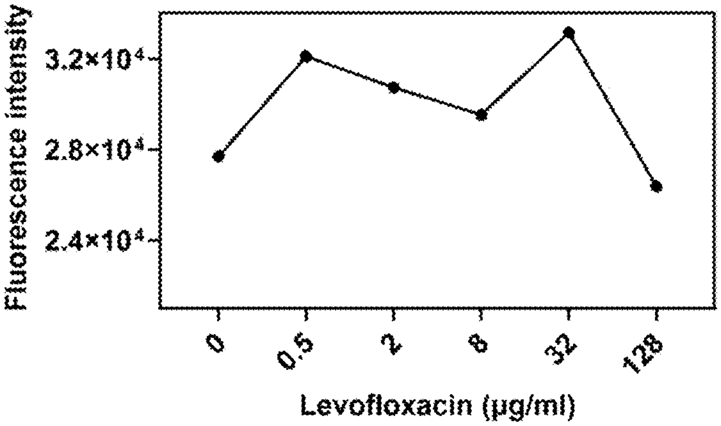
FIG. 12 shows the effect of levofloxacin (LEV) on bacteria contained in alveolar lavage fluid in the specific embodiment of the application.
Figure 13:
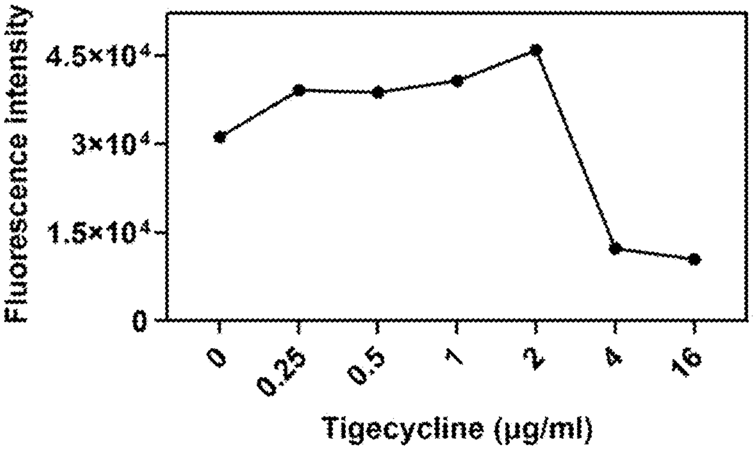
FIG. 13 shows the effect of tigecycline (TGC) on bacteria contained in alveolar lavage fluid in the specific embodiment of the application.
Figure 14:
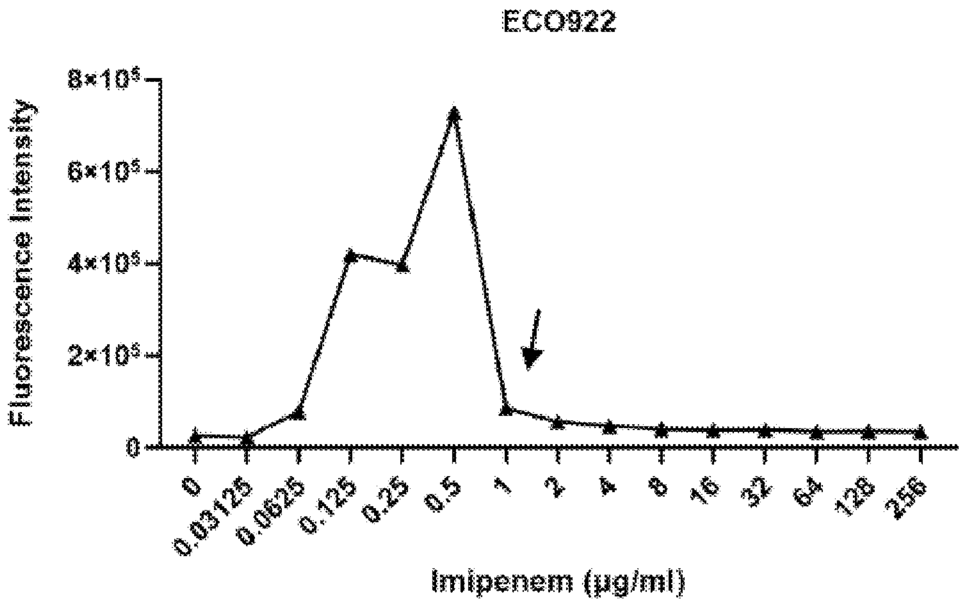
FIG. 14 shows the detection results of the effect of imipenem on *Escherichia coli* ECO922 by DAA-Tetra probe in the specific embodiment of the application.
Figure 15:
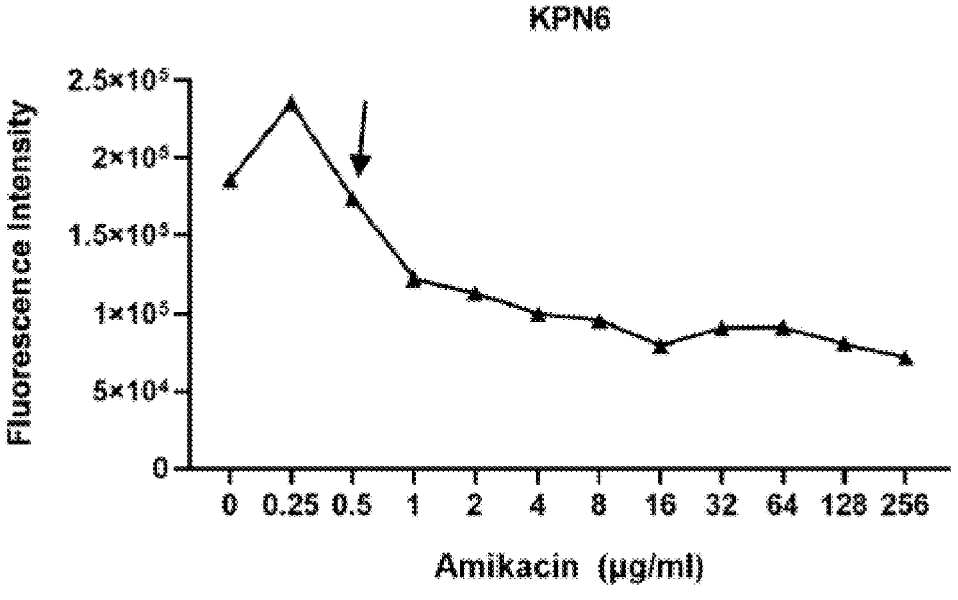
FIG. 15 is the test result of using DAA-Tetra probe to detect the effect of Amikacin on *Klebsiella pneumoniae* KPN6 in the specific embodiment of the application.
Figure 16:
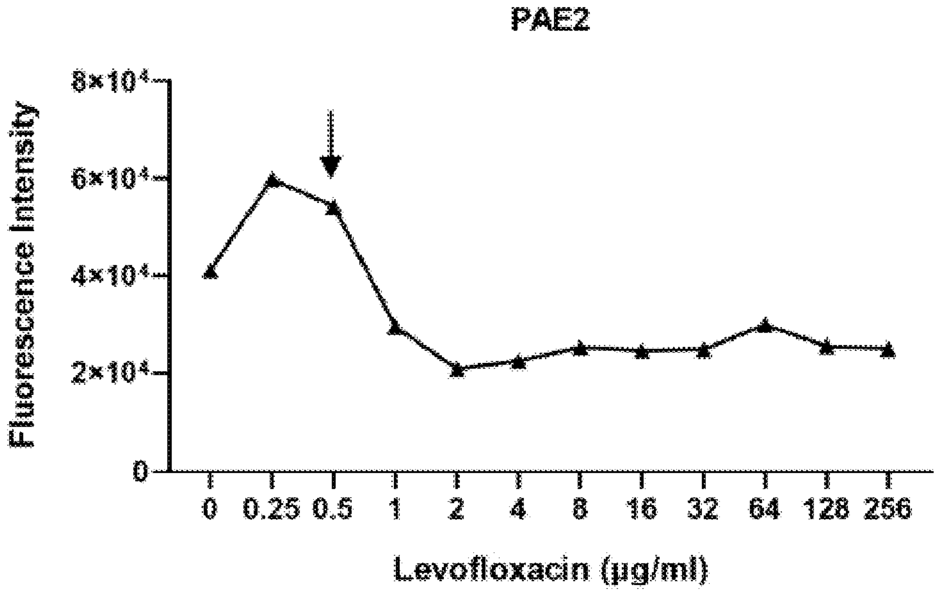
FIG. 16 shows the detection result of using DAA-Tetra probe to detect the effect of levofloxacin on *Pseudomonas aeruginosa* PAE2 in the specific embodiment of the application.
Figure 17:
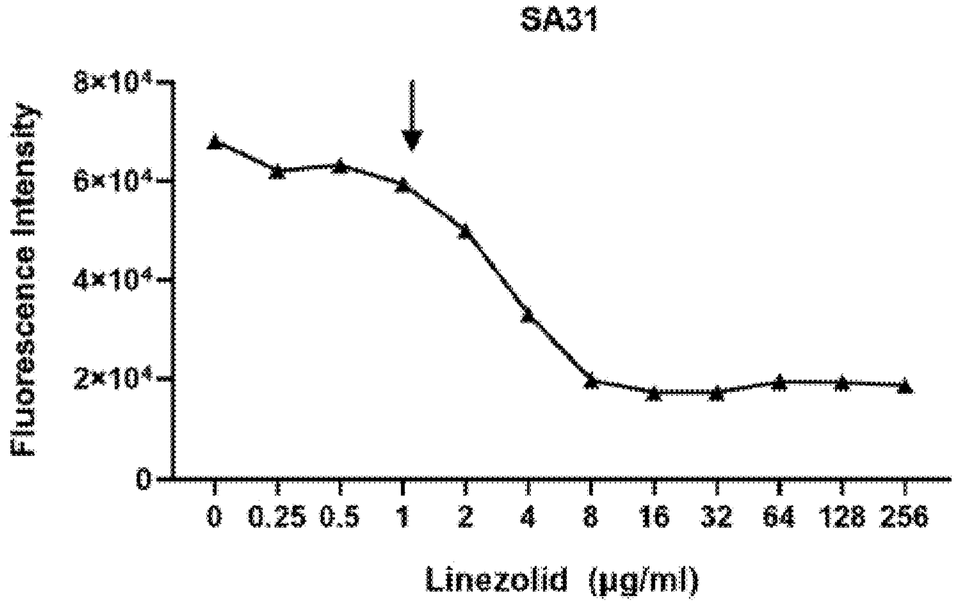
FIG. 17 is the test result of using DAA-Tetra probe to detect the effect of Linezolid on *Staphylococcus aureus* SA31 in the specific embodiment of the application.
Figure 18:
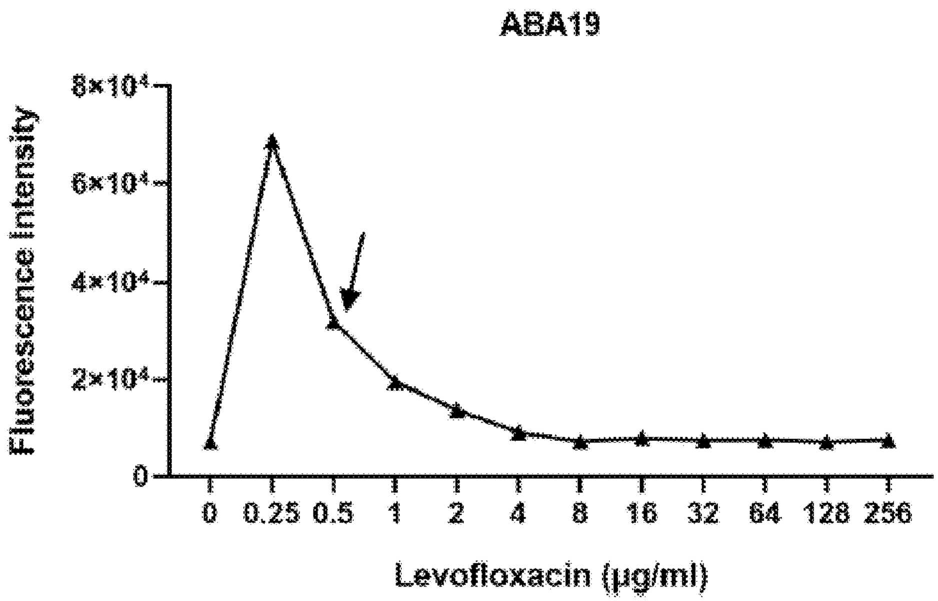
FIG. 18 is the test result of using DAA-Tetra probe to detect the effect of levofloxacin on *Acinetobacter baumannii* ABA19 in the specific embodiment of the application.
Figure 19:
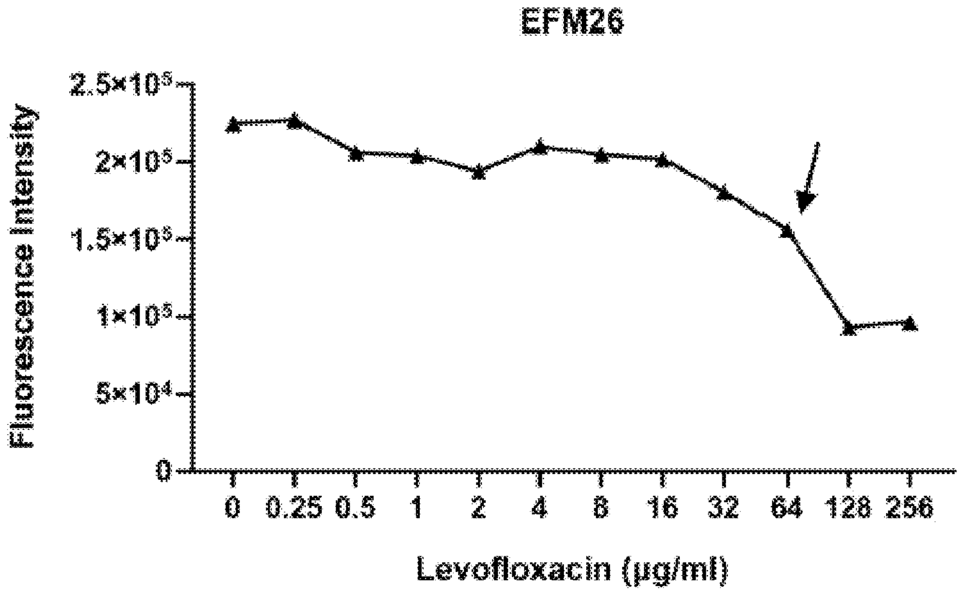
FIG. 19 is the test result of the effect of levofloxacin on *Enterococcus faecium* EFM26 detected by DAA-Tetra probe in the specific embodiment of the application.
Figure 20:
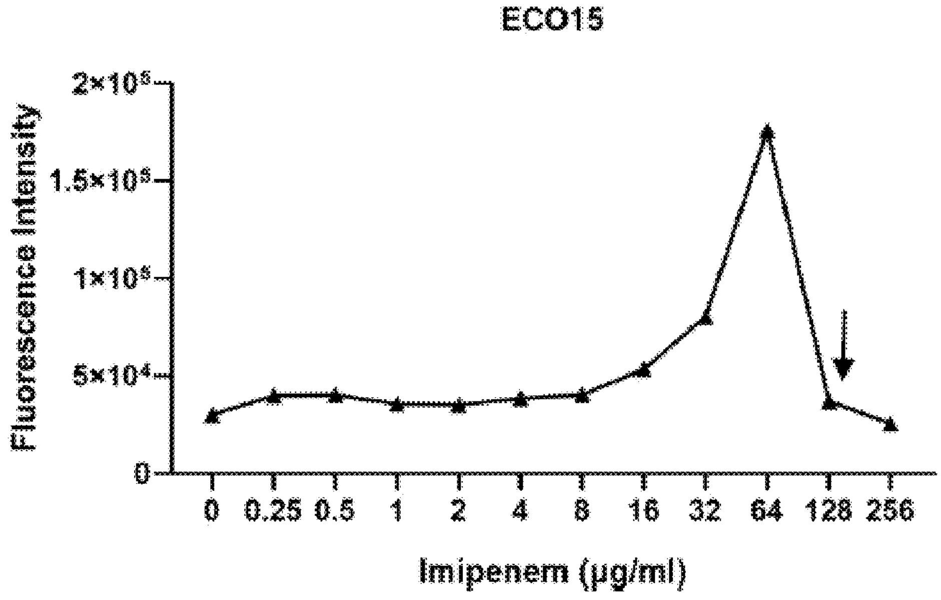
FIG. 20 is the result of using DAA-Cy5-2 to detect the effect of imipenem on *Escherichia coli* ECO15 in the specific embodiment of the application.
Figure 21:
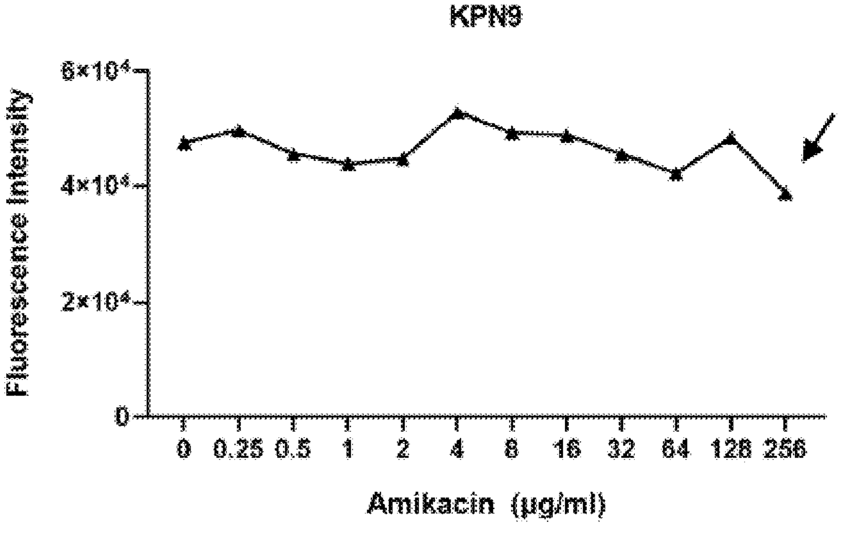
FIG. 21 shows the detection result of the effect of Amikacin on *Klebsiella pneumoniae* KPN6 detected by DAA-Cy5-2 probe in the specific embodiment of the application.
Figure 22:
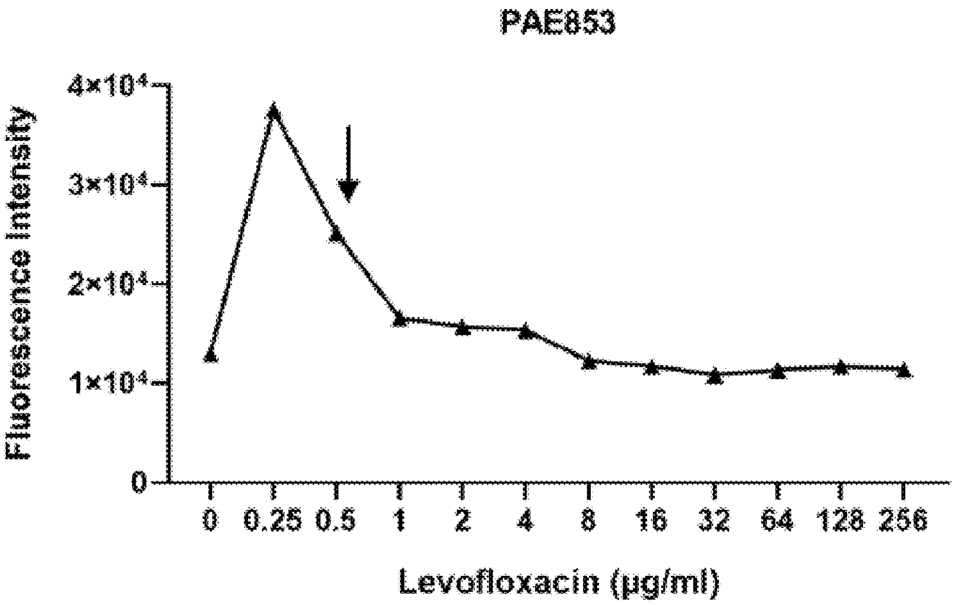
FIG. 22 is the detection result of the effect of levofloxacin on *Pseudomonas aeruginosa* PAE853 detected by DAA-Cy5-2 probe in the specific embodiment of the application.
Figure 23:
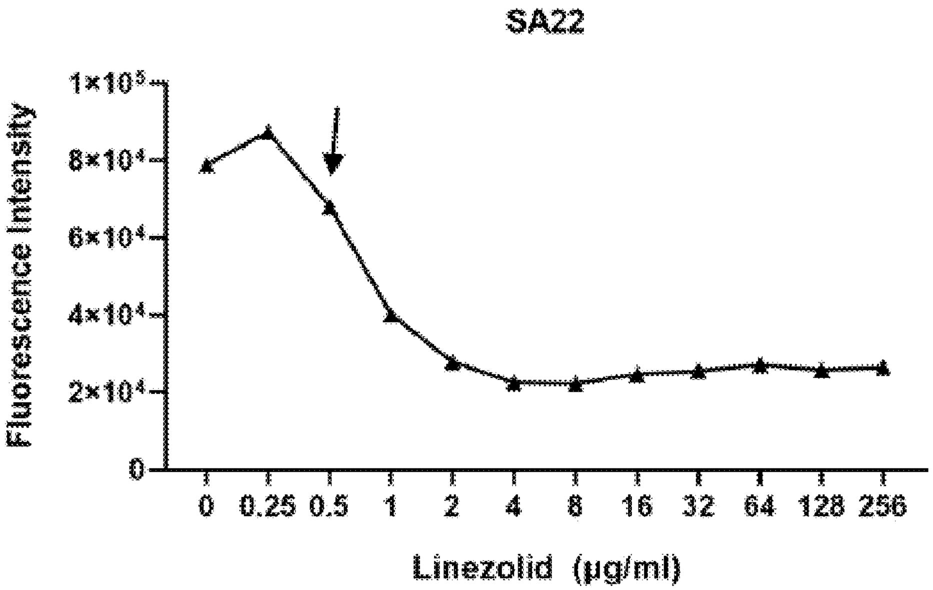
FIG. 23 is the test result of using DAA-Cy5-2 probe to detect the effect of Linezolid on *Staphylococcus aureus* SA22 in the specific embodiment of the application.
Figure 24:
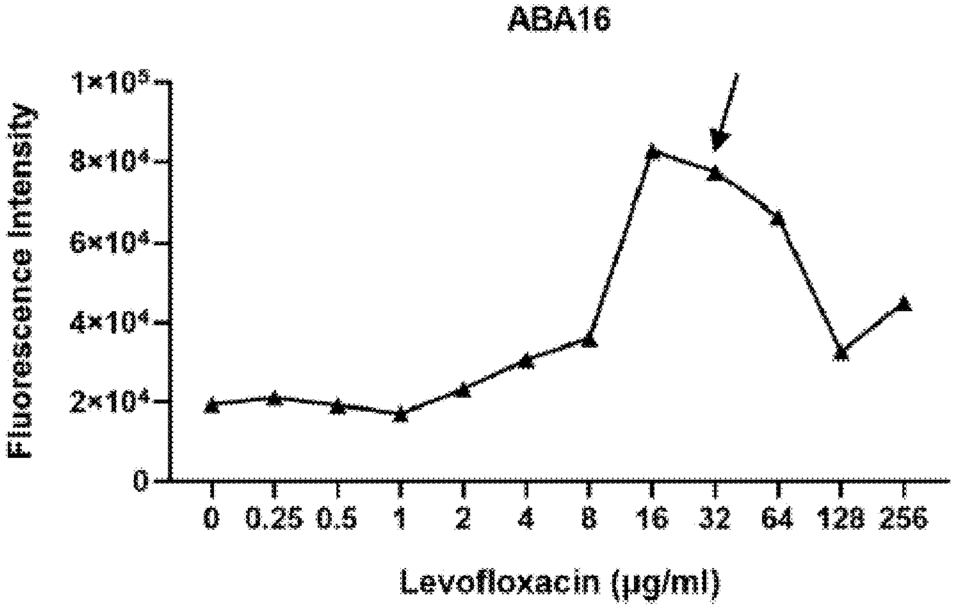
FIG. 24 is the detection result of the effect of levofloxacin on *Acinetobacter baumannii* ABA16 detected by DAA-Cy5-2 probe in the specific embodiment of the application.
Figure 25:
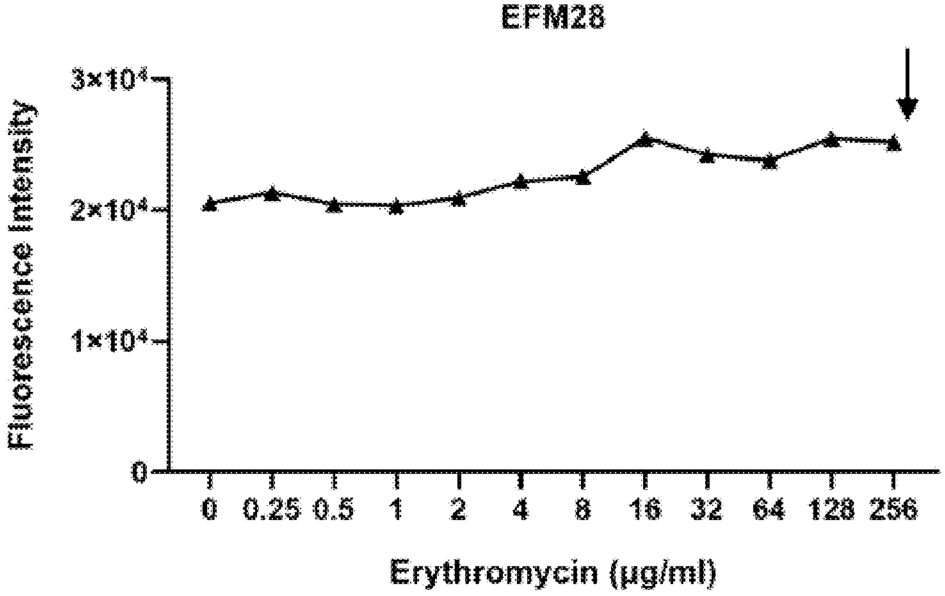
FIG. 25 is the test result of the effect of levofloxacin on *Enterococcus faecium* EFM28 detected by DAA-Cy5-2 probe in the specific embodiment of the application.

With reference to the flow chart of the rapid detection method of antimicrobial susceptibility test based on FDAA metabolic markers shown in FIG. 3, FDAA is used for the detection of antimicrobial susceptibility test of alveolar lavage fluid. The specific experimental steps are as follows:

1. Mix bronchoalveolar lavage fluid (BALF, 10 ml) of patients with hospital acquired pneumonia with cation regulated broth medium (CAMHB, 10 ml) of twice the concentration to prepare the bacterial fluid to be tested.
2. Add 45 µl antibiotic solutions of different concentrations to the 96-well plate separately (see Table 1 for antibiotic concentration gradient settings).
3. Add 50 µl of the bacterial solution prepared in step 1 to the 96-well plate and mix well.
4. Add 5 µl of 10 mM Cy5-DAA probe (final concentration 0.15 mM, see FIG. 1 for its structure) into each well, mix well, and then cultivate in dark for 2 hours.
5. Add 200 µl PBS solution for dilution, and then use flow cytometry to detect the fluorescence intensity of each sample. The flow detection results are shown in FIG. 11-13 (imipenem: IPM; Levofloxacin: LEV; Tigecycline: TGC).

Table 5 shows the comparison of the test results between the FDAA metabolic labeling method and the clinical common drug sensitivity test equipment Vitek; The results of the drug sensitivity test for alveolar lavage fluid obtained by the invention (fast detection method of antimicrobial drug sensitivity test based on FDAA metabolic marker) are in good agreement with those obtained by Vitek 2, a commonly used clinical drug sensitivity test device.

TABLE 5

Comparison between the results of FDAA metabolic labeling method and Vitek 2, a commonly used clinical drug sensitivity test device

| Antibiotic | MIC, FDAA (µg/ml) | MIC, Vitek (µg/ml) | Sensibility |
|---|---|---|---|
| IPM | ≥256 | ≥16 | R |
| LEV | ≥32 | ≥8 | R |
| TGC | 4 | 2 | S |

The results of antimicrobial susceptibility test of alveolar lavage fluid of seven patients using FDAA and BMD methods are shown in the following table. The drug-resistant bacteria are shown in bold.

| Sample | Types of | Levofloxacin | | Tigecycline | | Meropenem | | CAZ-AVI | | Linezolid | |
|---|---|---|---|---|---|---|---|---|---|---|---|
| mumber | Infections | BMD | FaAST | BMD | FaAST | BMD | FaAST | BMD | FaAST | BMD | FaAST |
| 0130 | *A. baumannii* | 64 | 64 | **2** | **2** | 64 | 32 | 32 | 64 | 64 | 64 |
| 0202 | Negative | — | No response | — | No response | — | No response | — | No response | — | No response |

-continued

| Sample mumber | Types of Infections | Levofloxacin BMD | Levofloxacin FaAST | Tigecycline BMD | Tigecycline FaAST | Meropenem BMD | Meropenem FaAST | CAZ-AVI BMD | CAZ-AVI FaAST | Linezolid BMD | Linezolid FaAST |
|---|---|---|---|---|---|---|---|---|---|---|---|
| 0203 | *K. pneumoniae* | **0.25** | **0.25** | **1** | **0.125** | **0.25** | **0.25** | **0.25** | **0.25** | 64 | 16 |
| 0204 | *A. baumannii* | **0.5** | **0.25** | **0.5** | **0.5** | **0.5** | **4** | **8** | **2** | 256 | 64 |
| 0206 | *A. baumannii* | 32 | 64 | **1** | 8 | 32 | 32 | 32 | 64 | 128 | 64 |
| 0219 | *A. baumannii* | 32 | 64 | **1** | 64 | 32 | 64 | 32 | 64 | 32 | 16 |
| 0226 | *K. pneumoniae* | **1** | **0.25** | **1** | **0.5** | **0.25** | **0.25** | **1** | **0.5** | 64 | 16 |
| Agreement rates (%) | | 100 | | 71.4 | | 85.7 | | 100 | | 100 | |
| Agreement rates of all (%) | | | | | | | | | | | 91.4 |

Example 6

DAA-Tetra probe was used to detect the effect of imipenem (*Escherichia coli* ECO922), amikacin (*Klebsiella* pneumoniae KPN6), levofloxacin (*Pseudomonas aeruginosa* PAE2, *Acinetobacter baumannii* ABA19, *Enterococcus faecium* EFM26), linezolid (*Staphylococcus aureus* SA31) and other antibiotics on bacteria. The structure of DAA-Tetra probe is as follows:

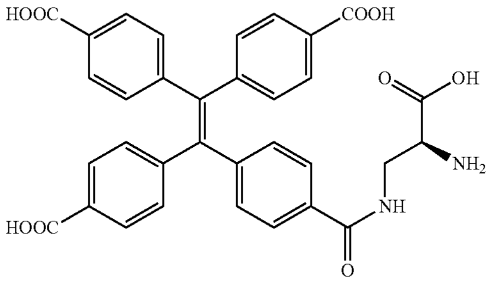 [SMILES: N[C@@H](CNC(=O)c1ccc(C(=C(c2ccc(C(=O)O)cc2)c2ccc(C(=O)O)cc2)c2ccc(C(=O)O)cc2)cc1)C(=O)O]

Excitation wavelength: 365 nm; Emission wavelength: 490 nm.

The specific experimental steps are as follows:

1. The tested colonies cultured overnight on the plate were picked and mixed thoroughly in 2× Cation-Adjusted Mueller Hinton Broth medium (2×CAMHB) to make bacterial suspension with turbidity of $OD_{600}$=0.1.
2. Add 45 μL antibiotic solutions of different concentrations to 96-well plates (the final concentration gradient is set to 0 μg/mL. 0.25 μg/ml. 0.5 μg/mL. 1 μg/ml. 2 μg/mL. 4 μg/ml. 8 μg/mL. 16 μg/mL. 32 μg/mL. 64 μg/mL. 128 μg/mL. 256 μg/mL).
3. Add 50 μL of the bacterial solution prepared in step 1 (the final concentration of the bacterial solution is $OD_{600}$=0.05) to the 96-well plate, and add 5 μL of 3 mM DAA-Tetra probe (the final concentration is 0.15 mM), mix well, and incubate in the dark at 37° C. 120 rpm for 2 hours.
4. After culture, dilute the mixed bacterial solution 10 times with PBS solution, and detect the fluorescence intensity of each sample with flow cytometry. The flow detection result is shown in FIG. 14-19, and the arrow is for the MIC value. The minimum inhibitory concentration of antibiotics was obtained according to the fluorescence signal intensity of flow detection, and the statistical results are shown in Table 6.

TABLE 6

Comparison of MIC test results of DAA-Tetra probe (hereinafter referred to as FaAST) and VITEK drug sensitivity test equipment

| | Gram negative bacteria | | | | Gram positive bacteria | |
|---|---|---|---|---|---|---|
| Bacteria | ECO922 | KPN6 | PAE2 | ABA19 | SA31 | EFM26 |
| Antibiotic | Imipenem | Amikacin | Levofloxacin | Levofloxacin | Linezolid | Levofloxacin |
| VITEK | 1 | 0.5 | 0.5 | ≤0.25 | 1 | ≥256 |
| FaAST | 1 | 0.5 | 0.5 | 0.5 | 1 | 64 |

Example 7

DAA-Cy5-2 probe was used to investigate the effect of imipenem (*Escherichia coli* ECO15), amikacin (*Klebsiella pneumoniae* KPN9), levofloxacin (*Pseudomonas aeruginosa* PAE853, *Acinetobacter baumannii* ABA16), linezolid (*Staphylococcus aureus* SA22), erythromycin (*Enterococcus faecium* EFM28) and other antibiotics on bacteria. The structure of DAA-Cy5-2 is shown below,

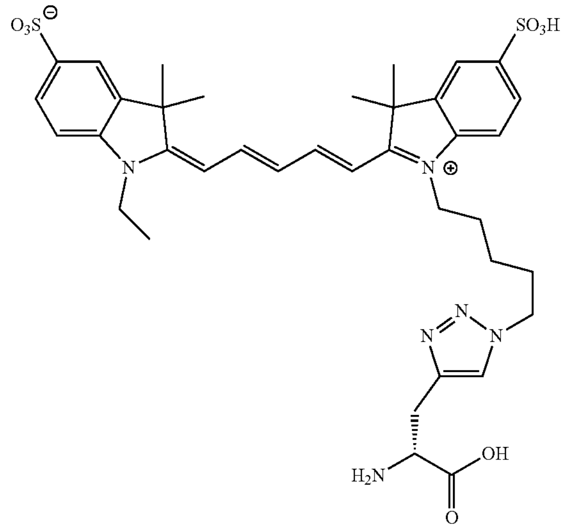

Excitation wavelength: 650 nm; Emission wavelength: 670 nm.

The specific steps are the same as in Example 5. The flow detection result is shown in FIG. 20-25, and the arrow shows the MIC value. The minimum inhibitory concentration of antibiotics was obtained according to the fluorescence signal intensity of flow detection, and the statistical results are shown in Table 7.

TABLE 7

Comparison of MIC test results of DAA-Cy5-2 probe (hereinafter referred to as FaAST) and VITEK drug sensitivity test equipment

| | Gram negative bacteria | | | | Gram positive bacteria | |
|---|---|---|---|---|---|---|
| Bacteria | ECO15 | KPN9 | PAE853 | ABA16 | SA22 | EFM28 |
| Antibiotic | Imipenem | Amikacin | Levofloxacin | Levofloxacin | Linezolid | Erythromycin |
| VITEK | 128 | 256 | 0.5 | 16 | 1 | ≥256 |
| FaAST | 128 | 256 | 0.5 | 32 | 0.5 | ≥256 |

The technical solution of the invention can realize the bacterial specific labeling fluorescence signal in a short time, detect the bacterial fluorescence signal intensity through the flow cytometer which has been widely used by laboratories and medical institutions at present, so as to quantitatively evaluate the bacterial drug sensitivity under the action of different antibiotic species and different antibiotic concentrations, which is a fast (3-4 h, 1.5-2.5 h MIC results can be obtained after improvement) The rapid detection method of antimicrobial susceptibility test is simple (simple operation, few steps, no need to use special equipment), sensitive (stable fluorescent labeling method, strong signal, high signal to noise ratio), accurate (detecting the metabolic activity of bacteria can effectively identify the bacteria in the state of non growth but metabolic activity (NGMA)), intuitive (good visualization), good compatibility with existing instruments (few instruments used, moderate price of instruments and more common), and easy to promote.

REFERENCES

[1] Syal K, Mo M, Yu H, et al. Current and emerging techniques for antibiotic susceptibility tests [J]. Theranotics, 2017, 7 (7): 1795

[2] Manina G, Dhar N, Mckinney J D. Stress and host immunity amplify *Mycobacterium tuberculosis* phenotypic heterogeneity and induce nongrowing metabolically active forms [J] Cell Host&Microbe, 2015, 17(1):32-46.

[3] Hou Z, An Y, Hjort K, et al. Time Lapse Investigation of Antibiotic Susceptibility Using a Microfluidic Linear Gradient 3D Culture Device [J] Lab on a Chip, 2014, 14(17):3409-3418.

[4] Choi J, Yoo J, Lee M, et al. A rapid antimicrobial susceptibility test based on single-cell morphological analysis [J] Science Translational Medicine, 2014, 6(267):267ra174-267ra174.

[5] Baltekin Boucharin A, Tano E, et al. Antibiotic susceptibility testing in less than 30 min using direct single-cell imaging [J] Proceedings of the National Academy of Sciences, 2017,114(34):9170-9175.

[6] Hou H W, Bhattacharyya R P, Hung D T, et al. Direct detection and drug-resistance profiling of bacteremias using inertial microfluidics [J] Lab on a Chip, 2015, 15(10):2297-2307.

[7] Bhattacharyya R P, Bandyopadhyay N, Ma P, et al. Simultaneous detection of genotype and phenotype enables rapid and accurate antibiotic susceptibility determination [J] Nature Medicine, 2019, 25(12):1858-1864.

[8] Longo G, Alonso Sardue L, Rio L M, et al. Rapid detection of bacterial resistance to antibiotics using AFM cantilevers as nanomechanical sensors [J] Nature Nanotechnology, 2013, 8(7):522.

[9] Tao Y, Wang Y, Huang S, et al. Metabolic-Activity-Based Assessment of Antimicrobial Effects by DZO-Labeled Single-Cell Raman Microspectroscopy [J] Analytical Chemistry, 2017, 89(7):4108-4115.

[0010] Hong W, Karanja C W, Abutaleb N S, et al. Antibiotic Susceptibility Determination within One Cell Cycle at Single-Bacterium Level by Stimulated Raman Metabolic Imaging [J] Analytical Chemistry, 2018, 90(6):3737-3743.

[0011] Yang K, Li H Z, Zhu X, et al. Rapid Antibiotic Susceptibility Testing of Pathogenic Bacteria Using Heavy-Water-Labeled Single-Cell Raman Spectroscopy in Clinical Samples [J] Analytical Chemistry, 2019, 91(9): 6296-6303.

[0012] Pidgeon S E, Fura J M, Leon W, et al. Metabolic Profiling of Bacteria by Unnatural C-terminated D-Amino Acids [J] Angew Chem Int Ed Engl. 2015, 54(21):6158-6162.

[0013] Erkin K, Srinivas T, Edward H, et al. Synthesis of fluorescent D-amino acids and their use for probing peptidoglycan synthesis and bacterial growth in situ [J] Nature Protocols. 2015, 10(1):33.

The invention claimed is:

1. A method for evaluating the metabolic activity of bacteria, comprising:

labeling a bacteria with a fluorescent D-type amino acid metabolic marker;

culturing the bacteria;

monitoring a fluorescence intensity of the fluorescent D-type amino acid metabolic marker during culturing; and evaluating a metabolic activity of the bacteria during culturing;

wherein monitoring comprises measuring the fluorescence intensity via flow cytometry.

2. The method of claim 1, wherein the fluorescent D-type amino acid metabolic marker comprises

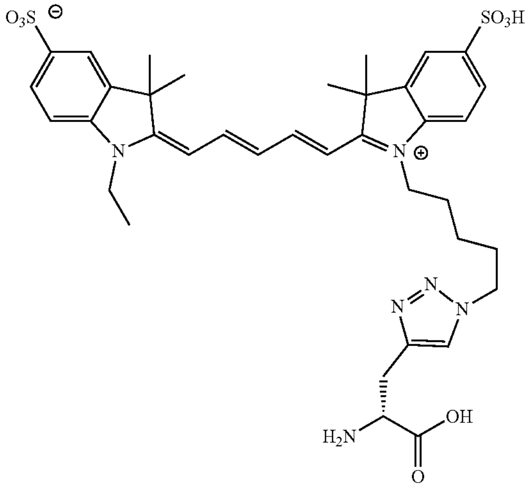

or

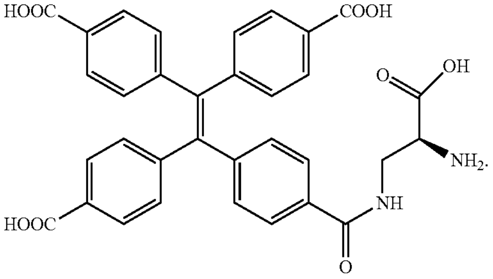

3. The method of claim 1, wherein the fluorescent D-type amino acid metabolic marker is a D-type amino acid or a derivative thereof, covalently modified by a fluorescent group.

4. The method of claim 1, wherein the fluorescent D-type amino acid metabolic marker comprises a D-type amino acid fluorescent probe selected from the group consisting of tetramethyl rhodamine (TAMRA), carboxyl fluorescein (FAM), Cyanine 5 (Cy5),

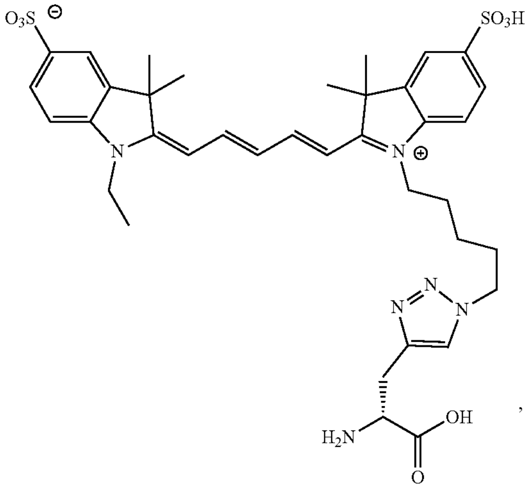

, or

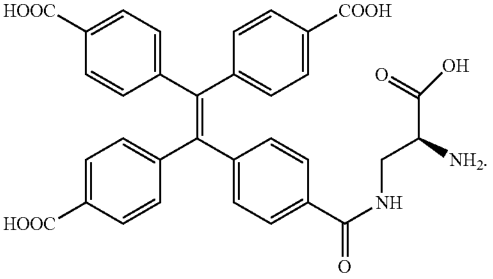

5. The method of claim 1, wherein the fluorescent D-type amino acid metabolic marker is derived from D-alanine or a derivative thereof and has the following structural formula:

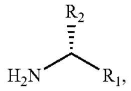

wherein $R_1$ is selected from

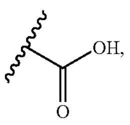 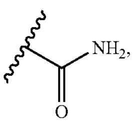 or 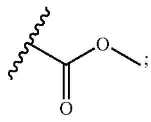

and $R_2$ is a fluorescent group.

6. A method for testing antimicrobial susceptibility, comprising:

mixing a fluorescent D-type amino acid metabolic marker with a test solution comprising a sample to be tested, thereby obtaining a first mixture;

adding an antibiotic solution to the first mixture, thereby obtaining a second mixture;

culturing the second mixture;

monitoring one or more fluorescence intensity of the fluorescent D-type amino acid metabolic marker during culturing; and evaluating an antimicrobial susceptibility activity of the sample during culturing;

wherein monitoring comprises measuring the one or more fluorescence intensity via flow cytometry; and wherein evaluating comprises determining the minimum inhibitory concentration of the antibiotic.

7. The method of claim 6, wherein the fluorescent D-type amino acid metabolic marker comprises

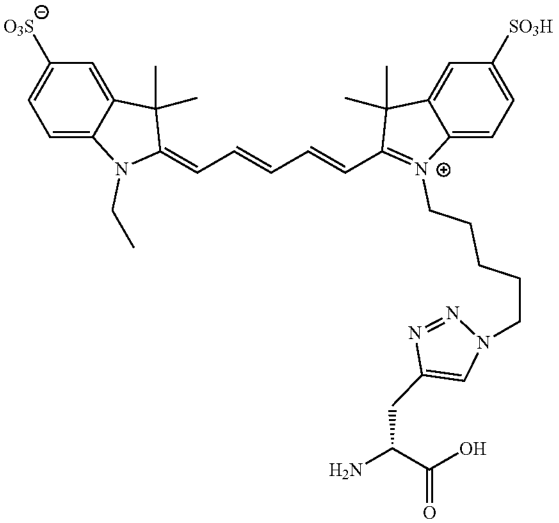

or

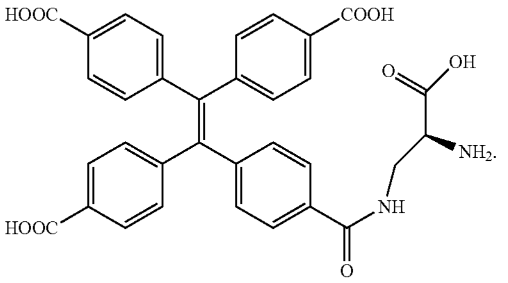

8. The method of claim 6, wherein the sample to be tested comprises alveolar lavage fluid and/or blood.

9. The method of claim 6, wherein the antibiotic has a gradient concentration, wherein the final concentration is 0.01 to 5 mM.

10. The method of claim 6, wherein the fluorescent D-type amino acid metabolic marker is a D-type amino acid or a derivative thereof, covalently modified by a fluorescent group.

11. The method of claim 6, wherein the fluorescent D-type amino acid metabolic marker comprises a D-type amino acid fluorescent probe selected from the group consisting of tetramethyl rhodamine (TAMRA), carboxyl fluorescein (FAM), Cyanine 5 (Cy5),

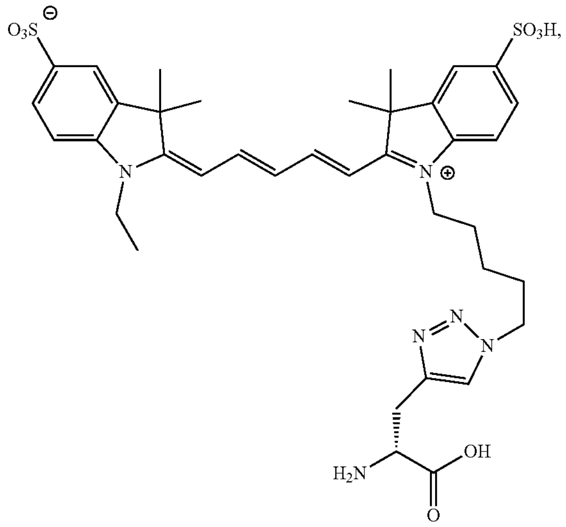

or

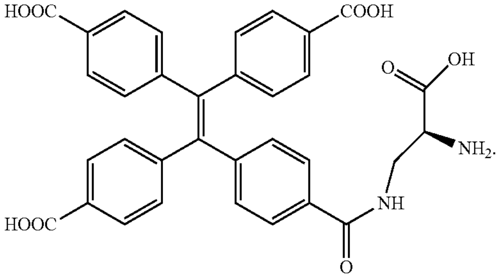

12. The method of claim 6, wherein the fluorescent D-type amino acid metabolic marker is derived from D-alanine or a derivative thereof and has the following structural formula:

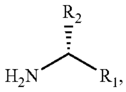

wherein $R_1$ is selected from

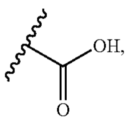 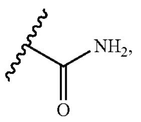 or 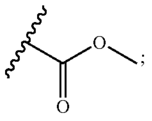

and $R_2$ is a fluorescent group.

13. The method of claim 6, wherein the antibiotic is selected from penicillins, cephalosporins, mercaptopenicillenes, aminoglycosides, tetracyclines, amide alcohols, macrolides, glycopeptides, sulfonamides, quinolones or nitroimidazoles.

* * * * *